(12) United States Patent
Kornowski et al.

(10) Patent No.: US 10,835,709 B2
(45) Date of Patent: Nov. 17, 2020

(54) MICROCATHETER TUBING ARRANGEMENT

(71) Applicant: Nitiloop Ltd., Herzlia (IL)

(72) Inventors: Ran Kornowski, Ramat-HaSharon (IL); Dvir Keren, Tel Aviv (IL)

(73) Assignee: Nitiloop Ltd., Herzlia (IL)

( * ) Notice: Subject to any disclaimer, the term of this patent is extended or adjusted under 35 U.S.C. 154(b) by 353 days.

(21) Appl. No.: 15/028,948

(22) PCT Filed: Nov. 4, 2014

(86) PCT No.: PCT/IL2014/050958
§ 371 (c)(1),
(2) Date: Apr. 13, 2016

(87) PCT Pub. No.: WO2015/063781
PCT Pub. Date: May 7, 2015

(65) Prior Publication Data
US 2016/0250443 A1    Sep. 1, 2016

Related U.S. Application Data

(60) Provisional application No. 61/899,335, filed on Nov. 4, 2013.

(51) Int. Cl.
*A61M 25/00* (2006.01)
*A61M 25/09* (2006.01)
(52) U.S. Cl.
CPC ...... *A61M 25/0023* (2013.01); *A61M 25/001* (2013.01); *A61M 25/0026* (2013.01); *A61M 25/0054* (2013.01); *A61M 25/0069* (2013.01); *A61M 2025/0042* (2013.01); *A61M 2025/09066* (2013.01)

(58) Field of Classification Search
CPC ........... A61M 2025/0042; A61M 2025/09066; A61M 25/001; A61M 25/0023; A61M 25/0026; A61M 25/0054; A61M 25/0069
See application file for complete search history.

(56) References Cited

U.S. PATENT DOCUMENTS

| | | | |
|---|---|---|---|
| 5,071,407 A | 12/1991 | Termin et al. | |
| 5,159,937 A | 11/1992 | Tremulis | |
| 5,380,304 A | 1/1995 | Parker | |
| 5,405,380 A | 4/1995 | Gianotti et al. | |

(Continued)

FOREIGN PATENT DOCUMENTS

| CN | 1689529 | 11/2005 |
|---|---|---|
| CN | 102300600 | 12/2011 |

(Continued)

OTHER PUBLICATIONS

Communication Relating to the Results of the Partial International Search Dated Feb. 23, 2015 From the International Searching Authority Re. Application No. PCT/IL2014/050958.

(Continued)

*Primary Examiner* — Brandy S Lee

(57) ABSTRACT

Attachment of tubes of various constructions for use in a microcatheter, including joining to a multifilar helix. Methods of uses and construction with concentric tubes axially displaceable over one another to control navigability and/or positioning properties of a microcatheter.

21 Claims, 15 Drawing Sheets

(56) References Cited

U.S. PATENT DOCUMENTS

| | | | |
|---|---|---|---|
| 5,456,667 | A | 10/1995 | Ham et al. |
| 5,480,382 | A | 1/1996 | Hammerslag et al. |
| 5,497,785 | A | 3/1996 | Viera |
| 5,814,062 | A | 9/1998 | Sepetka et al. |
| 5,911,715 | A | 6/1999 | Berg et al. |
| 6,036,670 | A | 3/2000 | Wijeratne et al. |
| 6,059,812 | A | 5/2000 | Clerc et al. |
| 6,464,632 | B1 | 10/2002 | Taylor |
| 6,652,508 | B2 | 11/2003 | Griffin et al. |
| 6,893,421 | B1 | 5/2005 | Larson et al. |
| 6,939,337 | B2 | 9/2005 | Parker et al. |
| 7,169,160 | B1 | 1/2007 | Middleman et al. |
| 7,833,218 | B2 | 11/2010 | Lunn et al. |
| 7,909,779 | B2 | 3/2011 | Shimogami et al. |
| 8,034,045 | B1 | 10/2011 | Lyons |
| 8,323,326 | B2 | 12/2012 | Dorn et al. |
| 8,343,136 | B2 | 1/2013 | Howat et al. |
| 8,460,213 | B2 | 6/2013 | Northrop |
| 2001/0034514 | A1 | 10/2001 | Parker |
| 2004/0006362 | A1 | 1/2004 | Schaefer et al. |
| 2005/0085846 | A1 | 4/2005 | Carrison et al. |
| 2005/0222585 | A1 | 10/2005 | Miyata et al. |
| 2009/0216200 | A1* | 8/2009 | Geis .................. A61M 25/0043 604/246 |
| 2010/0094258 | A1* | 4/2010 | Shimogami ......... A61M 25/005 604/527 |
| 2010/0160899 | A1 | 6/2010 | Gulachenski |
| 2011/0172520 | A1 | 7/2011 | Lentz |
| 2011/0178464 | A1* | 7/2011 | Rawls ............... A61M 25/0052 604/168.01 |

FOREIGN PATENT DOCUMENTS

| | | |
|---|---|---|
| EP | 0590407 | 4/1994 |
| EP | 0925801 | 6/1999 |
| EP | 1243283 | 9/2002 |
| EP | 1120127 | 8/2004 |
| EP | 2607724 | 6/2013 |
| JP | 2012-192177 | 10/2012 |
| JP | 2013-144006 | 7/2013 |
| WO | WO 92/14508 | 9/1992 |
| WO | WO 95/10317 | 4/1995 |
| WO | WO 2010/060889 | 6/2010 |
| WO | WO 2015/063781 | 5/2015 |

OTHER PUBLICATIONS

International Preliminary Report on Patentability Dated May 19, 2016 From the International Bureau of WIPO Re. Application No. PCT/IL2014/050958.
International Search Report and the Written Opinion Dated Apr. 20, 2015 From the International Searching Authority Re. Application No. PCT/IL2014/050958.
Asahi Intecc "Micro Catheter Corsair", Asahi Intecc Co., Medical Product, 1 P., Mar. 14, 2014.
Translation Dated Oct. 17, 2018 of Notice of Reasons for Rejection Dated Oct. 2, 2018 From the Japan Patent Office Re. Application No. 2016-525535. (3 Pages).
Notification of Office Action and Search Report Dated Aug. 1, 2018 From the State Intellectual Property Office of the People's Republic of China Re. Application No. 201480072194.4 and Its Summary in English. (13 Pages).
Notice of Reasons for Rejection Dated Oct. 2, 2018 From the Japan Patent Office Re. Application No. 2016-525535. (3 Pages).
Translation Dated Sep. 19, 2018 of Notification of Office Action Dated Aug. 1, 2018 From the State Intellectual Property Office of the People's Republic of China Re. Application No. 201480072194. 4. (13 Pages).
Decision of Rejection Dated May 7, 2019 From the Japan Patent Office Re. Application No. 2016-525535. (1 Page).
Communication Pursuant to Article 94(3) EPC Dated Apr. 12, 2019 From the European Patent Office Re. Application No. 14806453.8. (5 Pages).
Office Action Dated Dec. 4, 2019 From the Israel Patent Office Re. Application No. 245454 and Its Translation Into English. (6 Pages).

* cited by examiner

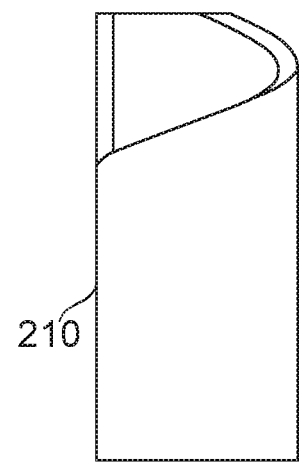
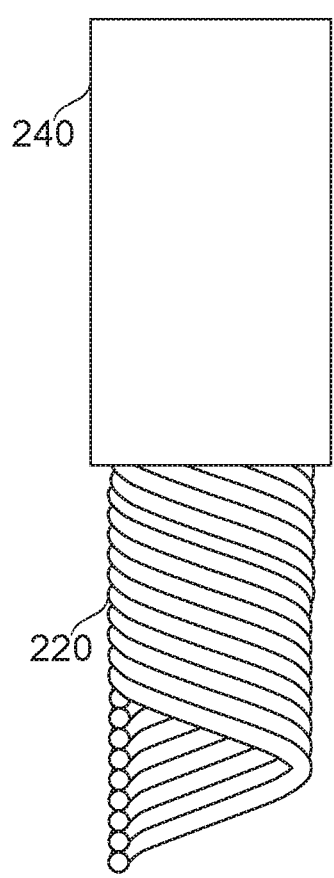
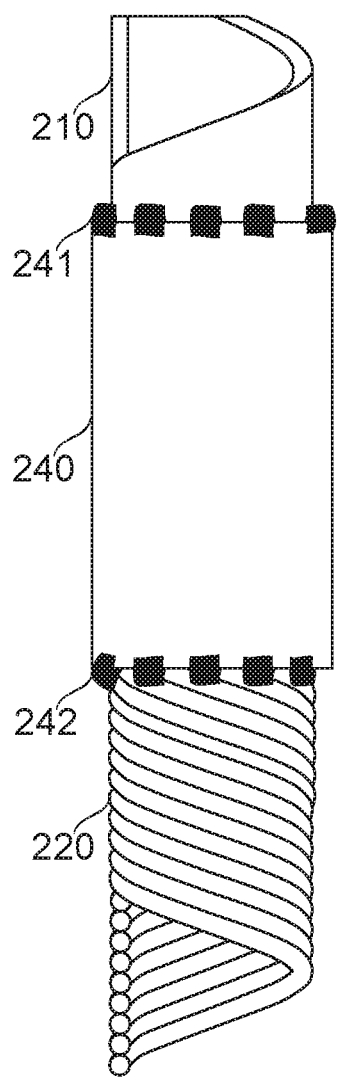
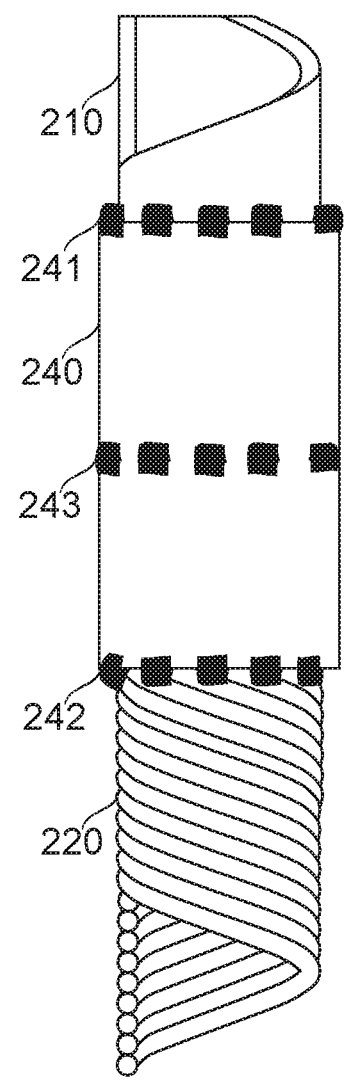
FIG. 4A   FIG. 4B   FIG. 4C

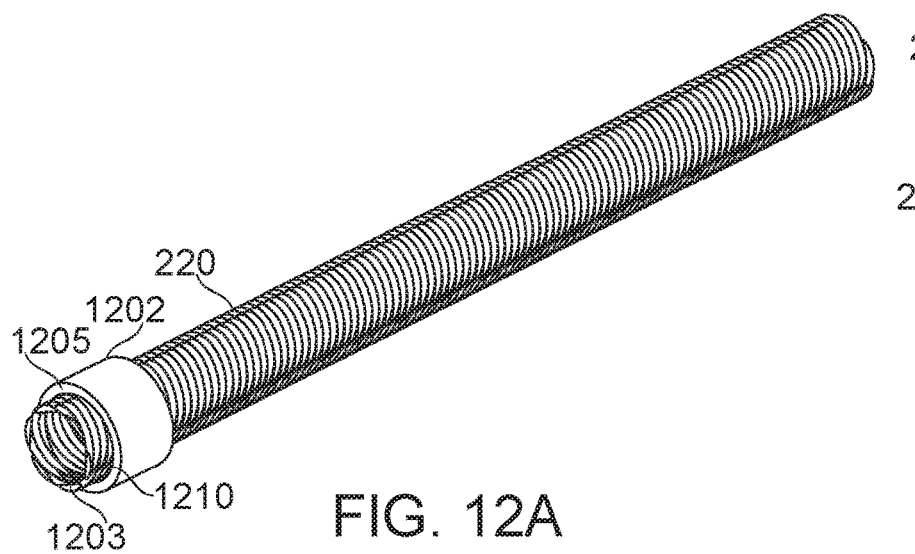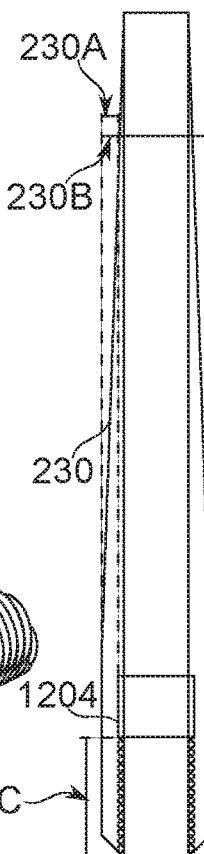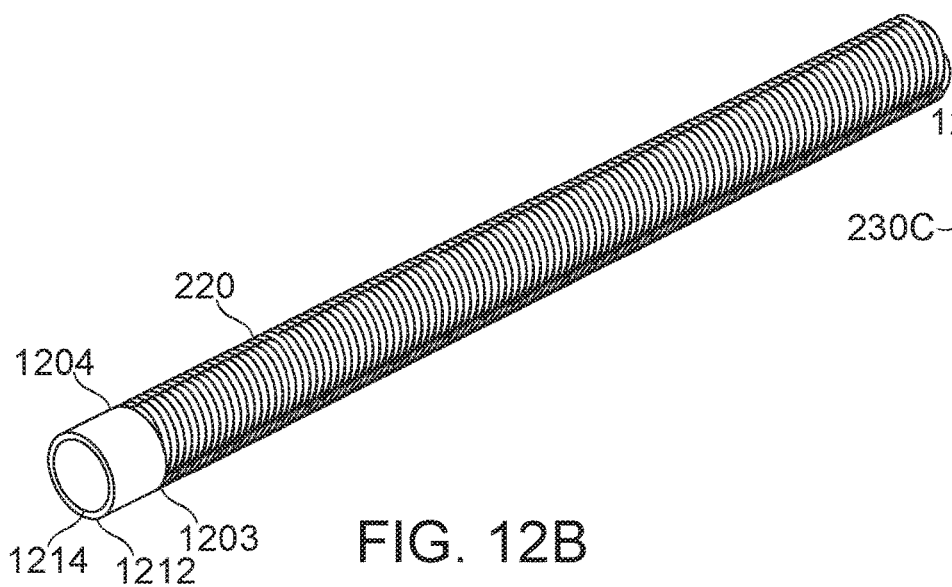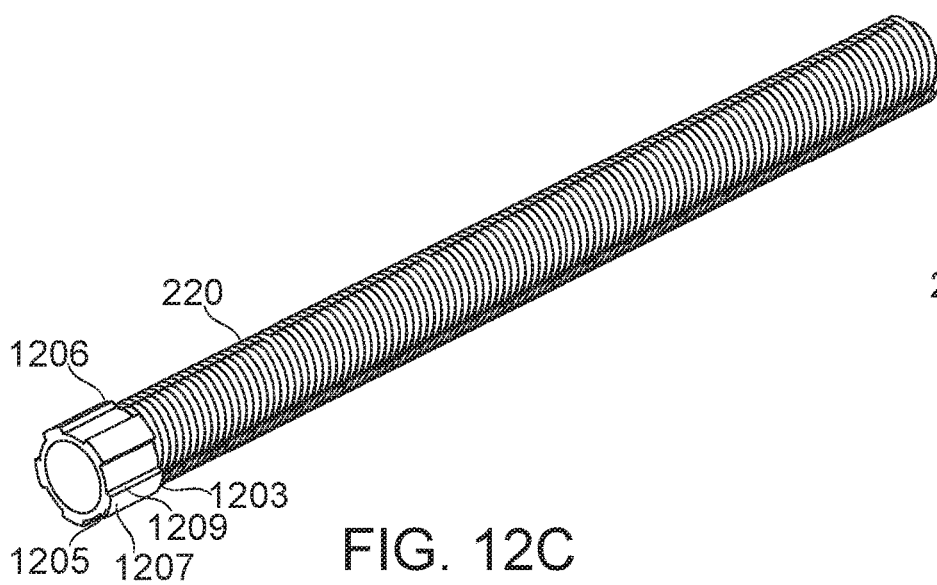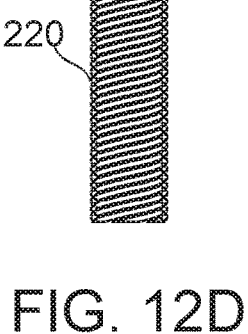

MICROCATHETER TUBING ARRANGEMENT

RELATED APPLICATIONS

This application is a National Phase of PCT Patent Application No. PCT/IL2014/050958 having International filing date of Nov. 4, 2014, which claims the benefit of priority under 35 USC § 119(e) of U.S. Provisional Patent Application No. 61/899,335 filed on Nov. 4, 2013. The contents of the above applications are all incorporated by reference as if fully set forth herein in their entirety.

FIELD AND BACKGROUND OF THE INVENTION

The present invention, in some embodiments thereof, relates to a medical device for insertion into vessels (e.g., arteries, Eustachian tubes, fallopian tubes), and/or the manufacture thereof. More particularly, but not exclusively, it relates to the determination of operating properties along the length of a device and/or methods of manufacture for achieving these properties.

Angioplasty is the technique of mechanically widening a narrowed or obstructed blood vessel, typically as a result of atherosclerosis. Angioplasty has come to include a range of vascular interventions typically performed in a minimally invasive or percutaneous method.

Angioplasty procedures are often performed over a guidewire which reaches to a site of intervention. The guidewire itself commonly requires support from a microcatheter in order to be moved into position.

In the current art, both axially and radially composite constructions of microcatheters have been described which attend to the problems of tracking the narrow, delicate, and potentially tortuous vascular anatomy which the guidewire must negotiate.

U.S. Pat. No. 7,909,779 relates to: "A catheter body includes a coil body which is formed by winding or stranding metal wires and having a distal portion and a proximal portion. The distance between coils adjacent to each other in the distal portion is greater than the distance between coils adjacent to each other in the proximal portion."

U.S. Pat. No. 6,652,508 relates to: "An intravascular catheter including a proximal stiff metallic tube and a distal flexible tube. A distal portion of the metallic tube has a portion removed to define a void (e.g., spiral slot) which decreases the stiffness of the metallic tube. A proximal portion of the distal flexible tube is disposed in the void to provide a secure connection and to blend the stiffness of the metallic proximal tube and the flexible distal tube without significantly increasing profile."

International Patent Publication No. WO2012160562 A1 by the Applicant relates to: " . . . a microcatheter comprising a deployment element disposed about around at least a portion of an exterior of a distal end of the microcatheter, the deployment element configured for repeatedly expanding and collapsing, the distal end arranged to allow forward or reverse axial displacement while the deployment element maintains a position, the deployment element arranged for positioning the microcatheter distal end approximately in the middle of a vessel."

SUMMARY OF THE INVENTION

According to an aspect of some embodiments of the present invention, there is provided a microcatheter trackable through a mammalian vasculature, comprising: an metal member defining a first lumen section and having an external diameter sized to pass into vascular lumen of less than 3 mm diameter; and a metallic helix defining a second lumen section; the metal member and the metallic helix comprising a region of end-to-end attachment defining an unobstructed passageway through the first and second lumen sections.

According to some embodiments of the invention, the metal member is elongated.

According to some embodiments of the invention, the passageway through the first and second lumen sections comprises a metal surface.

According to some embodiments of the invention, the region of end-to-end attachment comprises a connecting member attached to the exteriors of the metal member, and the metallic helix.

According to some embodiments of the invention, the connecting member defines a lumen containing portions of the metal member and the metallic helix.

According to some embodiments of the invention, the connecting member is metal.

According to some embodiments of the invention, the attachment is by welding.

According to some embodiments of the invention, the region of end-to-end attachment comprises a direct weld between the metal member and the metallic helical winding.

According to some embodiments of the invention, the first and second lumen sections are sized for the passage therethrough by a tubular lining.

According to some embodiments of the invention, the tubular lining is a plastic polymer.

According to some embodiments of the invention, the lining defines a lumen sized for passage of a guidewire.

According to some embodiments of the invention, the metallic helix comprises helically shaped metal wire.

According to some embodiments of the invention, the metal wire is circumferentially coated by a plastic polymer.

According to some embodiments of the invention, the metallic helix comprises a plurality of helically shaped wire filars.

According to some embodiments of the invention, the ends of the filars abutting the metal member are attached to one another.

According to some embodiments of the invention, the attachment is by welding.

According to some embodiments of the invention, all of the filar ends remain outside the diameter of the first lumen section at the region of abutting attachment.

According to some embodiments of the invention, the second lumen section has a passageway defined by the most interior portions of the filars, the smallest diameter of the passageway being substantially unchanged or increasing in axial cross-sections leading up to an end of the second lumen section within the region of end-to-end attachment.

According to some embodiments of the invention, the region of end-to-end attachment comprises portions of the first and second lumen sections axially aligned with one another.

According to some embodiments of the invention, the first and second lumen sections have diameters within 10% of one another at the region of end-to-end attachment.

According to some embodiments of the invention, the unobstructed passageway allows pushing of a guidewire tip freely therethrough.

According to some embodiments of the invention, the metal member comprises at least one externally positioned projection, the projection being fittingly received by the body of a tip member mounted at a distal end of the microcatheter, and fixed thereupon by the at least one projection.

According to some embodiments of the invention, the metal member comprises a radio-opaque material.

According to some embodiments of the invention, the radio-opaque material comprises at least one of the group consisting of gold, platinum, and tantalum.

According to some embodiments of the invention, a first thickness of a wall of the tip member overlying the projection is less than 50% of a second thickness of the wall over the ring away from the projection.

According to some embodiments of the invention, the at least one projection is circumferentially incomplete.

According to an aspect of some embodiments of the present invention, there is provided a method for attaching a tip to a microcatheter trackable through a mammalian vasculature, comprising: positioning a hollow helix comprising windings with regions of parallel contact within the lumen of a hollow polymer resin tip member such that each extends axially beyond an end of the other; and heating the material of the tip member such that it flows into spaces between the windings, only external to the regions of parallel contact.

According to some embodiments of the invention, the polymer resin tip member comprises radio-opaque particles embedded in the polymer resin.

According to some embodiments of the invention, the outer diameter of the hollow helix is less than 1.5 mm.

According to some embodiments of the invention, the outer diameter of the hollow helix is less than 1.1 mm.

According to an aspect of some embodiments of the present invention, there is provided a microcatheter trackable through a mammalian vasculature, comprising: a tip member, mounted at a distal end of the body of the microcatheter; the tip member being sized to pass into a vascular lumen of less than 3 mm diameter; the tip member comprising an angled receiving surface on a proximal side; the receiving surface being configured to receive a slideable member sliding distally along the body of the microcatheter; the receiving surface being sloped from a narrower to a wider diameter in a distal direction.

According to an aspect of some embodiments of the present invention, there is provided a method of preventing clotting in a region located radially between two concentric extended members, comprising: closing each the extended member at a distal end; and injecting a fluid carrier of anticoagulant into a proximal end of a lumen of a first of the extended members at least until the fluid reaches the region.

According to some embodiments of the invention, the fluid carrier crosses at least one aperture between the first extended member and the region.

According to some embodiments of the invention, the at least one aperture is between helical wire filars of the first extended member.

According to some embodiments of the invention, the injecting continues until the fluid is observable exiting a proximal end of the two concentric extended members.

According to some embodiments of the invention, the first extended member is internal to a second of the two concentric extended members.

According to some embodiments of the invention, the at least one aperture comprises at least one interstice between helical windings.

According to some embodiments of the invention, the second elongated member comprises a join between two elongated elements, and the gasket is fitted adjacent thereto.

According to some embodiments of the invention, the first elongated member is slideable over the gasket.

According to some embodiments of the invention, the ring comprises PTFE.

According to some embodiments of the invention, the restriction of the passage of blood comprises prevention of the proximal passage of blood under physiological pressure to form of a blood clot in the lumen of the first elongated member proximal to the gasket.

According to some embodiments of the invention, the restriction of the passage of blood comprises prevention of the proximal passage of blood under physiological pressure to fill the first elongated member proximal to the gasket.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIGS. 4A-4C illustrate assembly and attachment steps for joining assembly, according to some exemplary embodiments of the invention;

FIGS. 12A-12D show support rings attached to a distal portion of a microcatheter helix, according to some exemplary embodiments of the invention.

DESCRIPTION OF SPECIFIC EMBODIMENTS OF THE INVENTION

Figure 1A:
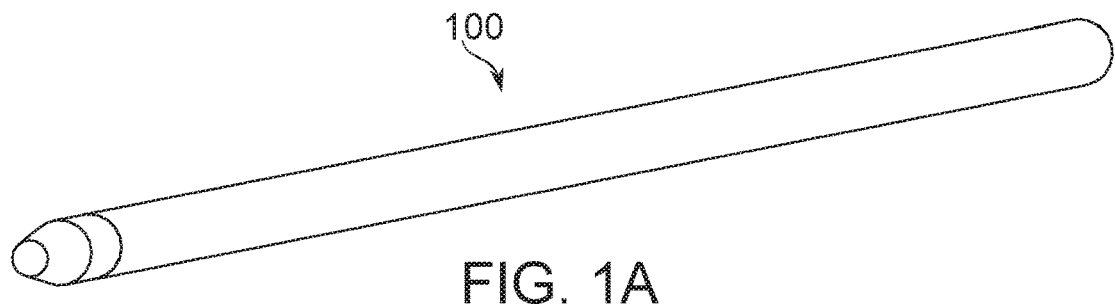
FIGS. 1A-1D provide overviews of components and subassemblies of a microcatheter, according to some exemplary embodiments of the invention.
Figure 1B:
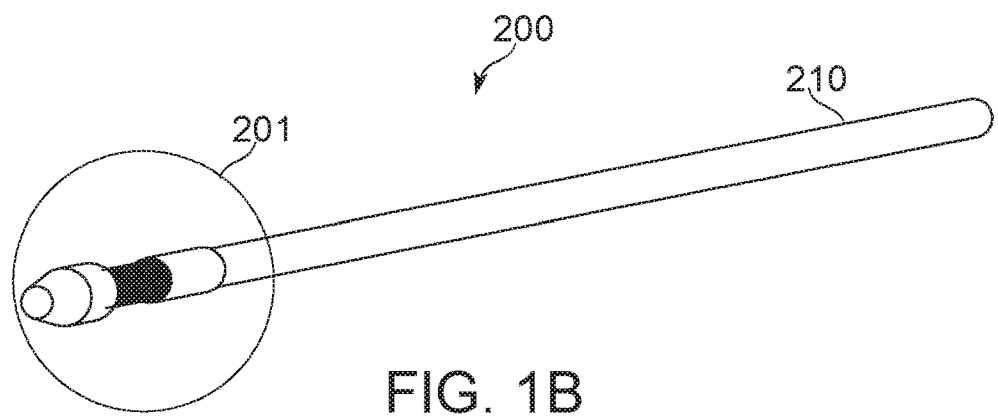
Figure 1C:
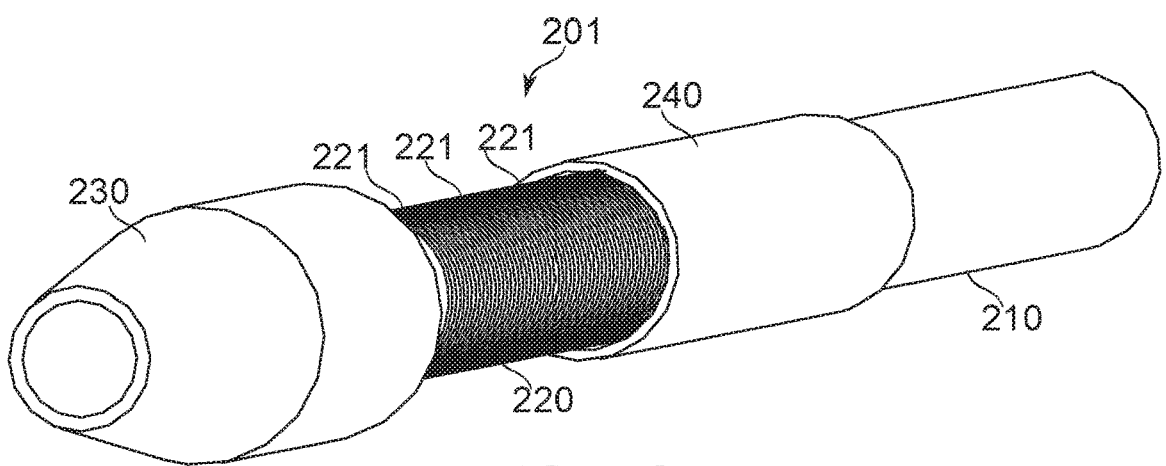
Figure 1D:
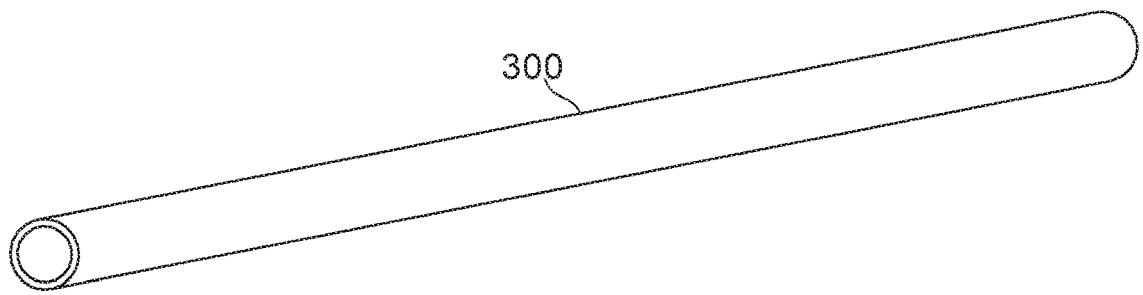

The present invention, in some embodiments thereof, relates to a medical device for insertion into vessels (e.g., arteries, Eustachian tubes, fallopian tubes), and/or the manufacture thereof. More particularly, but not exclusively, it relates to the determination of operating properties along the length of a device and/or methods of manufacture for achieving these properties.

Overview

A broad aspect of some embodiments of the invention relates to mechanical properties which vary along the length of a microcatheter, for example as determined by its manufacture and/or operation.

In some embodiments of the invention, a section along the length of the microcatheter comprises a helical portion defining a flexible lumenal wall. In some embodiments, the helical portion comprises a plurality of mutually interspaced wire filars, wound closely together around a common axis. A consequence, in some embodiments, of close-packing the wire filars is that they support one another in their inter-spaced positions to form an assembly of interlocked windings. As a microcatheter element, a close-packed, multifilar helix (also called herein a "multihelix") provides good maneuverability—including good torqueability and flexibility—while conferring resistance to kinking. A multihelix is sufficiently pushable to allow some existing microcatheter designs to use a multihelix from end to end, despite the cost this construction can entail.

In some embodiments of the invention, a section along the length of the microcatheter comprises a metal tube defining a lumenal wall. A metal tube gives good pushability and torqueability, but relatively poor maneuverability. It is available, however, in the form of relatively inexpensive hypotubing. In some embodiments, the microcatheter comprises a polymer tube extending along all or a section of its length. Polymer tubes are potentially inexpensive and flexible, but also potentially less pushable than metal tubes. In some embodiments, a polymer tube is reinforced (for example with metal braid), thickened, and/or combined with hypotubing to provide intermediate properties for pushability and navigability.

Microcatheters are a class of catheters used in body lumens which are generally distinguished by a small outer diameter (for example, 3 mm or less, depending on the intended use). Along with their small diameter, microcatheters, in some embodiments, comprise features of construction directed to the difficulties raised by navigation over relatively long distances (compared to their diameter) through potentially restricted and/or tortuous body lumens. In some embodiments of the invention, these features include, for example, a wall which is sufficiently flexible to navigate potentially non-predetermined tortuosities of a target lumen, sufficiently resilient that it is undamaged by this navigation, sufficiently smooth for unimpeded passage inside or outside of it, and/or sufficiently stiff that force exerted from outside the body is efficiently transmittable to the end of the microcatheter probe.

In some embodiments, the microcatheter lumen is sufficiently smooth and open to accommodate unimpeded passage of a guidewire or other insert of, for example, 200 μm to 700 μm diameter, or another larger or smaller diameter. In some embodiments, the microcatheter is navigable, for example, through a 1 cm radius turn, a 5 mm radius turn, or looser, tighter, or intermediate turn of, for example, at least 180°, at least 270°, at least 360°, or another larger, smaller, or intermediate angle. In some embodiments, the microcatheter is navigable to its target by steering and/or insertion force exerted at from, for example, 60-140 cm away from its distal end, or another range of larger, smaller, or intermediate distances. A torque applied to a proximal end of a microcatheter, in some embodiments, is transmitted to motion at the distal tip within, for example, 30° of twist, 60° of twist, 90° of twist, or another larger, smaller, or intermediate amount of twisting. The diameter of the microcatheter probe, in some embodiments of the invention, is, for example, 1 mm, 1.2 mm, 1.5 mm, 2 mm, 2.5 mm, 2.8 mm, a diameter which falls in a range between any two of the foregoing diameters, or another larger, smaller, or intermediate diameter.

An aspect of some embodiments of the invention relates to the sequential attachment along the length of a microcatheter of two differently constructed sections, such as a metal multihelix attached to a metal hypotube with a substantially matching inner diameter. Additionally or alternatively, sections comprising metal hypotubing of different construction (such as stainless steel and nitinol) are attached. In some embodiments, the attachment is end-to-end, and/or without mutual overlap between proximal and distal sections of the microcatheter. In some embodiments, the attachment is with two lumenal wall section ends abutting each other. In some embodiments, attachment brings the lumenal walls of two microcatheter sections into matched contact that avoids the formation of an impediment to passage through the lumen at the region of the join. In some embodiments, the join is formed such that the external profile of the join region does not comprise a widening that substantially impedes the navigability of the microcatheter through confined and/or tortuous vasculature.

It is a potential advantage to determine surgical performance characteristics of a microcatheter by varying properties along the microcatheter length. However, the process of manufacturing such a microcatheter can add significant complexity and cost to production. Combining separately made constructions into a single microcatheter potentially represents a relatively low-cost approach to achieving this advantage.

However—particularly when one of the constructions is a tightly wound multifilar helix with mutually supporting windings—such an approach raises challenges. Manufacturing the joint requires bringing two thin (several hundred μm)

and thin-walled (potentially less than 50 μm) flexible members into close and regular alignment, with little offset, and joining them.

The joint thus created furthermore represents a potential irregularity. In particular, but not exclusively, the end of a multifilar helix is prone to unraveling upon release, due to loss of mutual support at the free end, and/or due to release of residual stresses from manufacturing. The loose filar ends potentially intrude into the lumen, interfering with passage therethrough. Material added to a join in order to secure two parts together potentially creates bulk which can interfere with relative axial motion either inside or outside the microcatheter.

In some embodiments, microcatheter lumenal wall sections are brought into alignment for attachment by a connecting tube. In some embodiments of the invention, the abutting end of the helix tube is prepared by fixing the loose ends of the helix to the helix. In some embodiments, the fixing is by laser microwelding. Optionally, the connecting tube is directly attached to each of a helix tube (or other first tube) and a second tube. Optionally, the helix tube and the second tube are directly attached to one another. In some embodiments, the attachment is by laser microwelding. Potentially, the connecting tube adds strength, without creating an external irregularity that impairs microcatheter navigability.

In some embodiments of the invention, the connecting tube itself comprises the fill for welding attachment. Providing weld fill in tubular form potentially avoids the creation of irregularities due to different amounts of fill being provided at different weld points. Potentially, there is no need for further fill material to be added to the join. This is a potential advantage for passage of the microcatheter through the confined passages of the vasculature.

Potentially, the attachment described allows the microcatheter lumen in the region of attachment to be sufficiently smooth to allow passage of a guidewire without snagging or scratching. Preparation of the abutting face of the helix tube—in some embodiments—allows the tubes to join such that no wire protrudes into their common lumen. Optionally, the metal interior of the joined lumen remains exposed. This provides a potential advantage for the overall diameter of the microcatheter, by removing the need for a protective inner layer having sufficient mechanical strength to prevent a wire intrusion.

Potentially, this method of attachment diversifies the axial properties of a microcatheter with a reduced number of manufacturing steps, since the mechanical properties of each section are, in some embodiments, produced by the individual construction components as-is. In some embodiments, other manufacturing processes are applicable to refine the functional properties of the microcatheter portions.

Optionally, for example, the wires of the helix are pre-coated with a relatively thin coat of material before winding, for example, by dipping. Pre-coating can comprise, for example, a lubricious material such as Teflon® (Teflon® is a registered trademark of E. I. du Pont de Nemours and Company). In some embodiments, the winding coating is provided without additional protection or backing material. In some embodiments, welds made along the body of a helix extending away from the join comprise adjustments to the helix stiffness. Potentially, these adjustments distribute stress such that stresses applied near the join are at least partially absorbed by nearby portions of the microcatheter assembly.

An aspect of some embodiments of the invention relates to a reversibly retractable sheath and/or advanceable inner tube over a distal portion of the microcatheter tube.

In some embodiments of the invention, the assembled metal tubes are covered with a sheath. The sheath is made, for example, of polymer resin. In some embodiments, the sheath can be retracted from an inner portion of the microcatheter (or the inner portion advanced), potentially increasing maneuverability and/or altering other characteristics over the exposed inner section of the microcatheter. Optionally, for increased pushability, the sheath can advance again over the distal inner portion. As a potential advantage, this stiffens the distal tip, for example, to assist in crossing a blockage. In some embodiments of the invention, the relative motion of tubes is used to control another feature of the microcatheter, for example, a positioning device and/or steering mechanism.

An aspect of some embodiments of the invention relates to the attachment of a tube section of plastic material over an irregular outer surface portion of a microcatheter.

In some embodiments, for example, a tip for a microcatheter is secured to the end of a wire helix comprising the distal portion of a microcatheter. In some embodiments, the tip is secured by pressing and/or heating so that material of the tip intercalates into the surface gaps formed by the helical structure. In some embodiments, the tip comprises a radio-opaque substance, for example, a powder, for enhanced radiographic visualization.

An aspect of some embodiments of the invention relates to the attachment of a ring at the distal tip region of a microcatheter.

In some embodiments, a ring is attached to multihelix structure at a distal tip region of a microcatheter; for example as an application of structures and/or methods comprising attachment, such as end-to-end attachment, of a metal multihelix to a solid-walled metal cylinder, described herein.

In some embodiments, the ring provides features of, for example:
 support of movement, orientation, and/or stiffness for a tip member (such as a plastic tube, which can be provided as an atraumatic tip);
 anchoring of a tip member to the microcatheter; and/or
 radio-opaque marking.

A ring structure is optionally configured for anchoring by the provision of one or more protrusions which shape-lock an over-molded or otherwise fitted tip member into place. Shape locking comprises, for example, restriction of movement axially and/or circumferentially (rotationally). Optionally, anchoring by the ring structure allows reduction of the length of an anchoring region provided with a tip, potentially with advantages for reduced size and/or controlled flexibility of the tip member and/or distal tip region.

In some embodiments, the ring material comprises radio-opaque material such as gold, platinum, and/or tantalum. Potentially, this allows visualization of the position and/or movement of the tip, for example, under fluoroscopy. In some embodiments, the ring is circularly asymmetric (for example, comprising regions of greater and lesser thickness), such that rotation of the ring is visualized as changes in tip radio-opacity under fluoroscopic visualization.

In some embodiments, a ring is attached end-to-end with a distal end of a multihelix assembly. Optionally, the ring outer and/or inner diameters are about flush with the corresponding diameters of the multihelix. Optionally, this allows a greater range (compared, for example, to an over-fitted ring) for selection of the diameter and/or wall thickness of a tip member. For example, a ring section is thinner, allowing a greater tip wall thickness for the same tip diameter, a smaller tip diameter for the same tip wall thickness, or an intermediate compromise. Potentially, this allows selection of tip member thickness, sufficient for resisting collapse during navigation, together with small size and/or flexibility, enabling passage through targeted small and/or tortuous vascular structures.

In some embodiments, a ring comprises one or more external projections extending along the axis of the microcatheter, to which a portion of tip member is fitted such that rotational and/or axial movement of the tip is prevented. As a tip anchor, a ring provides a potential advantage over tip attachment to a multihelix, as the ring section can be provided with anchoring structure designed and manufactured apart from the specialized manufacturing process and structural constraints of a multihelix. Potentially, this allows greater control of tolerances and/or design of anchoring structures without hindrance from the grooving pattern of a multihelix. Potentially, anchoring is more stable to a solid ring piece, relative to a flexible multihelix. The use of end-to-end abutting attachment of ring and multihelix, in some embodiments, allows more of the available tip wall thickness to be devoted to anchoring and stabilization, by keeping the ring body that bears the anchoring projection thinner. Projections can take any of several shapes, for example, longitudinal along the axis of the ring, circumferential, lattice-like, circular, or other. In some embodiments, a pattern of projections is provided (for example a set of longitudinal projections around a ring circumference). In some embodiments, a single projection (such as a bump or pillar) serves as a tip anchor. It is to be understood that "projection" is relative to a minimum outer diameter; thus, in some embodiments, anchoring is alternatively described as being by provision of one or more depressed regions in the ring body, for example, a hole and/or slot into which material of the tip member is pressed.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Reference Microcatheter Embodiment

Reference is now made to FIGS. 1A-1D, which provide overviews of components and subassemblies of a microcatheter, according to some exemplary embodiments of the invention.

In some embodiments of the invention, microcatheter 100 comprises an internal element 200, and an overtube 300. In some embodiments, internal element 200 comprises four portions (detailed in region 201): proximal tube 210, multihelix 220, connector tube 240, and tip 230.

In some exemplary embodiments of the invention, multihelix 220 comprises a plurality of interlocking helical windings 221, extending along the length of multihelix 220. In some embodiments, proximal tube 210 comprises a flexible tube of solid stainless steel construction, for example, hypodermic tubing. In some embodiments, overtube 300 comprises a polyamide sheath.

The multihelix 220 and proximal tube 210 comprise a common inner lumen, in some embodiments of the invention, the lumen being adapted for passage of a guidewire. It should be noted that lumen smoothness is important for passage of a guidewire through a microcatheter. In an exemplary operating scenario, a 300 µm diameter guidewire is pushed through a lumen of approximately 500 µm diameter along a length of up to 150 cm. This entails pushing a flexible member that is, for example, thousands of times longer that it is wide. Even a partial sidewall obstruction may be impassable, if, for example, the tip encounters it while under bending force.

In some embodiments, the microcatheter itself is navigable to pass smoothly through potentially tortuous blood vessels without causing trauma. In some embodiments, the smallest vessel which the microcatheter passes into has a lumen of no larger than 3 mm. In some embodiments, the diameter of the lumen of the smallest vessel into which the microcatheter passes is 2.5-3.5 mm, 1.5-2.5 mm, 1-2 mm, 0.75-1.5 mm, or another larger or smaller inner diameter. In some embodiments, larger-diameter lumens are navigable on the way to a smallest distal vessel. In some embodiments, the distal tip of the microcatheter is navigable through at least 180° of a turn of radius 3-5 cm, 2-4 cm, 1-2 cm, 0.5-1.0 cm, or another larger or smaller turn radius.

Thus, assembling a connection between two microcatheter tube construction types is not only a matter of effecting attachment, but of effecting attachment without interfering with function. The small diameters of the parts concerned potentially increases the challenge of mating the ends.

Catheter Portion Connection

Figure 2A:
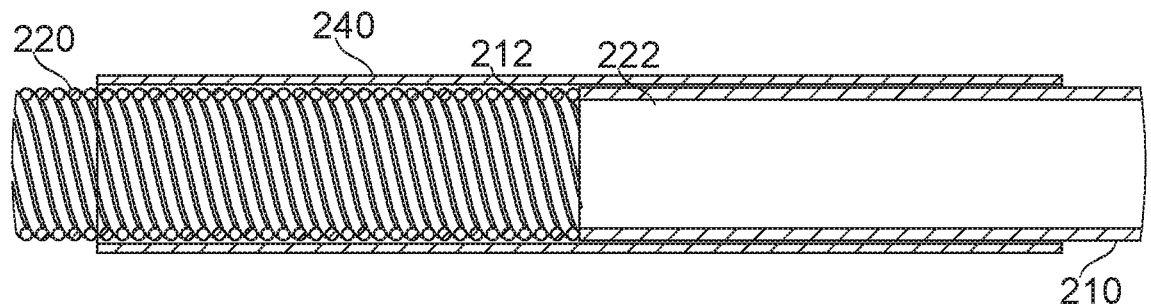
FIG. 2A illustrates attachment between a multihelix and a solid-walled proximal tube using a connector, according to some exemplary embodiments of the invention.

Reference is now made to FIG. 2A, which illustrates attachment between a multihelix 220 and a solid-walled proximal tube 210, made using a connector 240, according to some exemplary embodiments of the invention.

In some embodiments, connector 240 bridges between multihelix 220 and proximal tube 210. In some embodiments of the invention, aligned mating between multihelix 220 and proximal tube 210 is ensured by the relative sizes of the inner lumen of connector 240 and the outer diameters of tubes 220, 210. According to the embodiment, the tolerance of relative positioning of inner lumens 212, 222 is for example, 1-5 µm, 4-10 µm, 5-15 µm, 10-20 µm, 15-30 µm, or another larger or smaller tolerance range. In some embodiments, the specified difference between the inner diameter of connector 240 and the outer diameter of multihelix 220 and/or proximal tube 210 is about 20 µm. In some embodiments, the tolerances of manufacturing for connector 240, multihelix 220, and/or proximal tube 210 is about 10 µm, or a larger or smaller tolerance, consistent with the roles of assembly and/or connection as described herein. In some embodiments, the inner diameters of proximal tube 210 and multihelix 220 are matched, for example, within 10% of each other. In some embodiments, the matching is within ±0-2% of each other, ±1-5%, ±4-8%, ±6-12%, ±8-14%, or another relative diameter matching. Within these tolerances, in some embodiments, either the multihelix 220 or the proximal tube 210 is larger. In some embodiments, the multihelix 220 has a larger inner diameter by 10-15%, 12-18%, 15-20%, or another larger relative size.

In some embodiments of the invention, multihelix 220 comprises a wire helix structure. A multihelix or multifilar structure, in some embodiments, comprises at least one, and typically between 8 and 12 individual wires wound in inter-spaced helices aligned to a common axis. In some embodiments, the helices are wound to the same diameter. In some embodiments, the windings are close-fitted, and interlock to form a self-stabilizing structure. The wire helices are comprised, for example, of a metal alloy such as stainless steel, nitinol, or cobalt-chrome.

In some embodiments, the length of multihelix 220 is relatively short. For example, in a trans-femoral cardiac procedure, multihelix 220 is, for example 30 cm. Alternatively, multihelix 220 is 5-10 cm, 7-17 cm, 15-25 cm, 20-30 cm, 25-40 cm in length, or another longer or shorter length.

In some embodiments, the outer diameter of multihelix 220 is about 0.63 mm. In some embodiments, the inner diameter is about 0.51 mm. In some embodiments, the outer diameter of multihelix 220 is a diameter known in the art for constructing multihelices used intravascularly, for example, 0.55-0.65 mm, 0.7-0.9 mm, 0.85-0.95 mm, or 0.9-1.1 mm. In some embodiments, the wire filars forming the walls of the multihelix have a circular cross-section, and are, for example, 35-46 µm in diameter, 40-60 µm in diameter, 55-75 µm in diameter, 70-90 µm in diameter, 85-90 µm in diameter, 90-100 µm in diameter, or another larger or smaller diameter. Wires of mutually-differing diameter and/or wires with another cross-sectional shape (for example, square, rectangular, or oval) are used in some embodiments of the invention. The pitch to which wires are wound in some embodiments, is, for example, 1.7-1.9 mm, in the case of an 8-filar multihelix, or another larger or smaller pitch, according to a method of multihelix construction known in the art. It is to be understood that the wall thickness of the multihelix 220 is potentially fractionally larger than the wire filar thickness, due, for example, to irregularities in winding, so long as the irregularities do not impede functions such as the advancement of a guidewire through the lumen of multihelix 220.

Potential advantages of a multihelix construction over a solid tube construction include flexibility and/or kink resistance. Flexibility is potentially enhanced, for example, by windings configured to slide or separate under force. Kink resistance is potentially enhanced, for example, by the difficulty of concentrating force on an individual winding segment, and/or by restorative forces from other windings tending to push displaced windings back into position.

With respect to torqueability, wire filar multihelix construction in some embodiments has a higher specific torqueability in one direction than in another. For example, the direction of turning that tends to tighten the helix due to distal torque resistance has a higher torqueability than the direction that tends to helix unwinding. It is a potential advantage to concentrate multihelix construction in the distal portions of a microcatheter, where less distal torque resistance is received than in proximal portions.

In some embodiments of the invention, proximal tube 210 comprises a solid-walled metal tube. Potential advantages for push strength and torque transfer are derived from this construction. In some embodiments, the tube comprises stainless steel. Such a construction potentially provides good pushability (for example, a relatively high buckling resistance for its diameter). In some embodiments, the proximal tube 210 comprises another metal alloy. Optionally, the metal alloy is nitinol, which—for a particular geometry of construction—potentially provides increased flexibility, in exchange for a decrease in stiffness. In some embodiments, proximal tube 210 is itself a multihelix constructed, for example, as described with respect to multihelix 220 hereinabove. Additionally or alternatively, the tube distal to proximal tube 210 is another solid-walled metal tube. Optionally, the solid walls of the metal tube comprise modifications such as perforations made before or after joining. It should be noted that the methods of attachment described herein and the devices produced thereby are potentially transferable to other constructions and/or combinations of elongated structures suitable for use in a microcatheter, modified as necessary by one skilled in the art working based upon descriptions provided herein.

In some embodiments, the length of proximal tube 210 is chosen to be about the same as the length required to reach the end of portions of the vascular anatomy which are relatively straight, for example, having a larger radius of curvature than vessels near the distal target of the microcatheter. The length chosen can depend, for example, on the size of the patient, the chosen entry point for the microcatheter, and/or the length of guiding catheter through which the microcatheter must pass. For example, in a trans-femoral cardiac procedure, proximal tube 210 is about 118 cm in length. According to the embodiment, proximal tube 210 is 50-70 cm, 60-90 cm, 80-110 cm, 105-125 cm, or 120-140 cm in length, or another shorter or longer length.

In some embodiments of the invention, the proximal tube 210 outer diameter, wall thickness, and lumen diameter are sized to match tolerances for matching with the multihelix abutting end listed hereinabove. In some embodiments of the invention, the outer diameter of the proximal tube is about 0.63 mm. In some embodiments, the inner diameter of the proximal tube is about 0.53 mm. In some embodiments, the outer diameter of the proximal tube is 0.5-0.65 mm, 0.6-0.75 mm, 0.7-0.9 mm, 0.85-0.95 mm, 0.9-1.1 mm, or another larger or smaller outer diameter. In some embodiments, the wall thickness of proximal tube 210 is, for example, 30-50 µm, 40-50 µm, 45-60 µm, 50-70 µm, 60-80 µm, or another larger or smaller wall thickness. While the methods of joining disclosed herein are, in some embodiments, described with respect to tubes having circular lumens, the methods are in general applicable to lumens of other cross-sectional shapes, changed as necessary by one skilled in the art working based on the descriptions provided herein.

In some embodiments, the inner diameter of proximal tube 210 is less than the inner diameter of multihelix 220. The difference is small enough, however, that a guidewire remains passable through the proximal tube 220. The difference in dimensions is potentially an advantage to ensure that tolerances of alignment do not result in a narrowing step for navigation between the proximal tube 210 and the multihelix 220.

In some embodiments of the invention, connector 240 is a tube internally sized to accommodate an end of proximal tube 210 and an abutting end of multihelix 220. In some embodiments, connector 240 comprises stainless steel. In some embodiments, connector 240 is nitinol or another metal alloy. The length of connector 240 may be, for example, 5-7 mm, 5-10 mm, 7-15 mm, 10-20 mm, or another longer or shorter length. It is a potential advantage for the tube to be short enough that microcatheter navigability (considered relative to vessels which the join region must navigate) is unimpaired.

In some embodiments, connector 240 has an outer diameter of about 0.74 mm. In some embodiments, the inner diameter is about 0.65 mm. In some embodiments of the invention, connector 240 has a substantially uniform inner diameter, sized to accommodate the two abutting ends and align them within the tolerances specified hereinabove. In some embodiments of the invention, a portion of connector 240 is adjusted in inner diameter (for example, swaged) to accommodate proximal tube 210 having a different outer diameter from multihelix 220, while maintaining their inner lumens in alignment. In some embodiments of the invention, the thickness of the wall of connector 240 is, for example, 25-45 µm, 40-60 µm, 50-80 µm, 60-100 µm, or another larger or smaller thickness. It is a potential advantage for the connector 240 to be thick enough to provide structural strength to the joining region. Optionally, the wall thickness is selected to be thin enough, however, so that it does not make the microcatheter too itself too thick or irregular to navigate to the point which the join must reach during a surgical procedure.

Figure 2B:
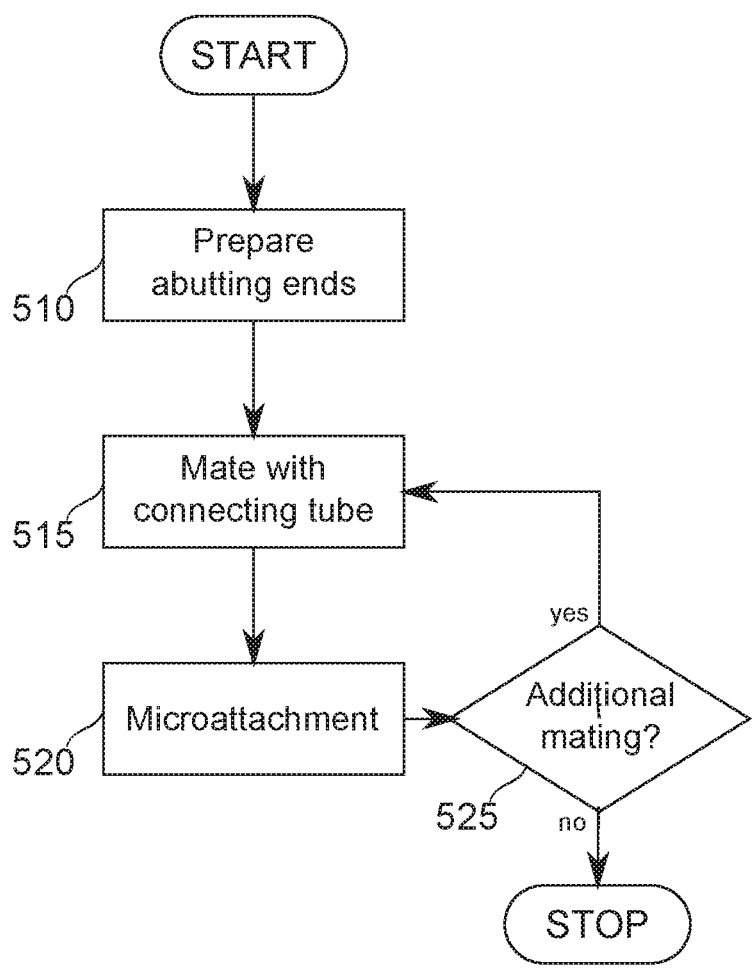
FIG. 2B is a flowchart of assembly of a microcatheter subassembly by joining of proximal tube and multihelix, according to some exemplary embodiments of the invention.

Reference is now made to FIG. 2B, which is a flowchart of assembly of a microcatheter subassembly by joining of proximal tube 210 and multihelix 220, according to some exemplary embodiments of the invention. Reference is further made to FIGS. 3A-3B and FIGS. 4A-4C, which illustrate phases in the joining assembly, according to some exemplary embodiments of the invention.

The flowchart begins, and at block 510, the abutting ends of the join are prepared. In some embodiments of the invention, lengths of proximal tubing, multihelix, and connector tubing are provided according to specifications described hereinabove.

In some embodiments, the tube end is previously cut by conventional means, potentially introducing fraying, splaying, compression or other damage in the process. Even if the previous cut is accomplished cleanly, there is a potential for a free end to become unraveled during handling. A wire from the helix-wound tube protruding into the microcatheter lumen can potentially block, snag, or scratch and hook a guidewire so that its operation is impeded. Portions of a guidewire thus damaged potentially themselves become an impediment to movement, jamming the microcatheter lumen.

It should be noted that at a free end of a multihelix, scratching by the wire filar ends is potentially less problematic, since the filars are free to deflect away from a passing guidewire. Where there is a fixed join, however, a potential problem has been recognized by the inventors whereby the filar end is prevented from deflection, making damage of a passing guidewire more probable.

In some embodiments of the invention, the abutting end 223 of multihelix 220 is prepared by an initial step of laser microwelding (FIG. 3A) which welds free ends of the wire filars 221 to one another, the weld points 224 being far enough back from end 223 that the wires 221 are in their axially aligned condition. In some embodiments, adjoining strands of the helical tube are welded together around a circumference some distance from the end, for example, 2-3 mm, 3-5 mm, 5-10 mm, or another larger or smaller distance from the end. In some embodiments, the welding is continuous around the circumference. In some embodiments, the welding is partial, for example 25%, 40%, 50%, or 80% of the circumference. In some embodiments, welding comprises direct welding of wire filars to each other, without the use of a separate welding wire. In some embodiments welding wire is used; however, it is a potential advantage to avoid the use of welding wire, since this avoids adding extra bulk to the welded region which may interfere with navigability and/or passage of items through the microcatheter lumen. In some embodiments, the size of the welded spot and/or of the laser spot cross-section is, for example, 25-35 µm, 30-45 µm, 40-60 µm, 50-70 µm, 65-75 µm, or another larger or smaller spot size. In some embodiments, the duration of laser illumination for each weld spot is about 1-3 msec, or a longer or shorter duration. In some embodiments, a welding machine's intensity is controlled by a voltage setting, and the voltage setting is between about 150-200 V, but potentially a higher or lower voltage. It should be understood that these welding machine settings are exemplary, and vary for different laser welding machines according to parameters which can be determined by one skilled in the art without undue experimentation, according to the descriptions provided herein.

Figure 3A:
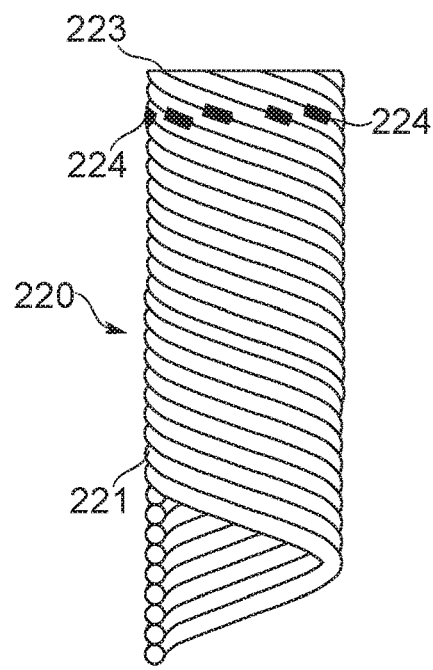
FIGS. 3A-3B illustrate preparation of a multihelix end for joining assembly, according to some exemplary embodiments of the invention.
Figure 3B:
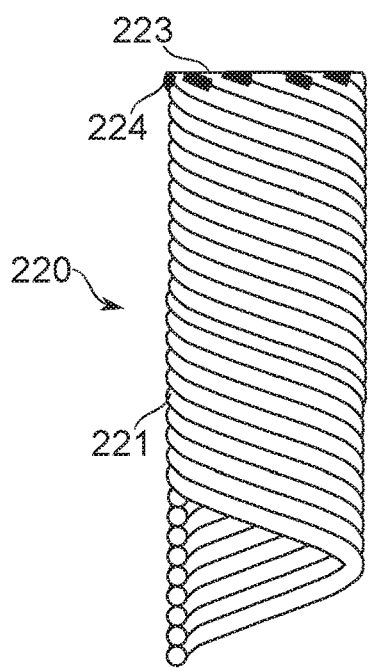

In some embodiments of the invention, the abutting end 223 is cut back to near the points 224 of welding, for example by grinding ablation (configuration of FIG. 3B). Grinding ablation may be performed, for example, by a Dremel® tool (Dremel® is a registered trademark of Robert Bosch Tool Corporation), a disk grinder, and/or by means of another tool, such as one that provides for a moving metal backing for an ablative powder of diamond or another hard material. The approach to the welding region is, for example, within 0-50 µm, 25-100 µm, 75-200 µm, any distance in between, or within a larger or smaller distance. In some embodiments, the result is a flat end of tightly bundled helix wires, which are held in place so that they do not intrude into the lumen where they would for a potential obstruction to a guidewire.

In some embodiments of the invention, the abutting end of the proximal tube 210 is prepared by grinding it back to evenness in preparation for join assembly. In some embodiments, tube 210 is roughened to receive attachment from connector 240.

For example, the external surface of the abutting end of tube 210 is mechanically scored and/or abraded, and/or pitted by laser energy.

At block 515—continuing in the flowchart of FIG. 2B—the connector tube 240 is mated (FIG. 4A) over at least one of the proximal tube 210 or the multihelix 220. In some embodiments of the invention, all tubes are first fitted together before attachment is performed. In some embodiments, fitting and attachment is performed one side at a time.

At block 520, microattachment is performed. In some embodiments of the invention, microattachment is by laser microwelding, for example, as described with respect to microwelding of the multihelix filars, hereinabove. A potential advantage of microwelding is that it adds no or very little additional thickness to the connection region, while forming a strong, direct, and controlled bond.

In some embodiments, welds 241 connect connector 240 to proximal tube 210. In some embodiments, welds 242 connect connector 240 to multihelix 220. In some embodiments of the invention, material of connector 240 is used as fill in connections 243 which directly join proximal tube 210 and multihelix 220. In some embodiments, the size of the welds is about 20-200 µm across, or another larger or smaller size. It is a potential advantage to perform welding without the use of welding wire to avoid adding bulk to the finished join.

In some embodiments, attachment comprises a shape-locking attachment. For example, connector 240 is melted in some embodiments to intercalate into the windings of multihelix 220, and/or to lock against irregularities in the end of proximal tube 210. In some embodiments, attachment is by another means, such as shrink- or expansion-fitting. For example, a nitinol or other metal connector tube is expanded at one temperature (and/or the connected tubes themselves shrunk), and the connection achieved by a shrink- or expansion fitting. In some embodiments, a polymer coating or adhesive comprises a portion of the material involved in tube attachment. In some embodiments, additional welds, laser heating, and/or laser cutting is applied to the microcatheter in regions extending away from the join. Potentially, welds along the multihelix add stiffness, providing a potential advantage for stress distribution away from the join region. Also providing a potential advantage for stress distribution, heating away from the join may change, for example, a stiffness of a metal due to heat effects on an alloy structure and/or due to ablation, cutting, or other redistribution of material.

At block 525, a determination is made if additional mating/microattachment steps are required. In some embodiments, additional attachment is required, for example, if only one of proximal tube 210 or multihelix 220 was connected during an earlier round of mating and microattachment. If more attachment is required, the flow chart returns to block 515. Otherwise, the flowchart ends.

Figure 4D:
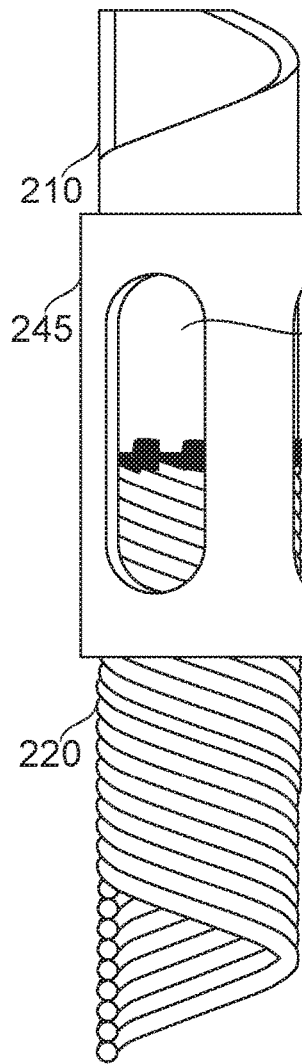
FIGS. 4D-4F show attachment configurations of a multihelix and a proximal tube, according to some exemplary embodiments of the invention.
Figure 4E:
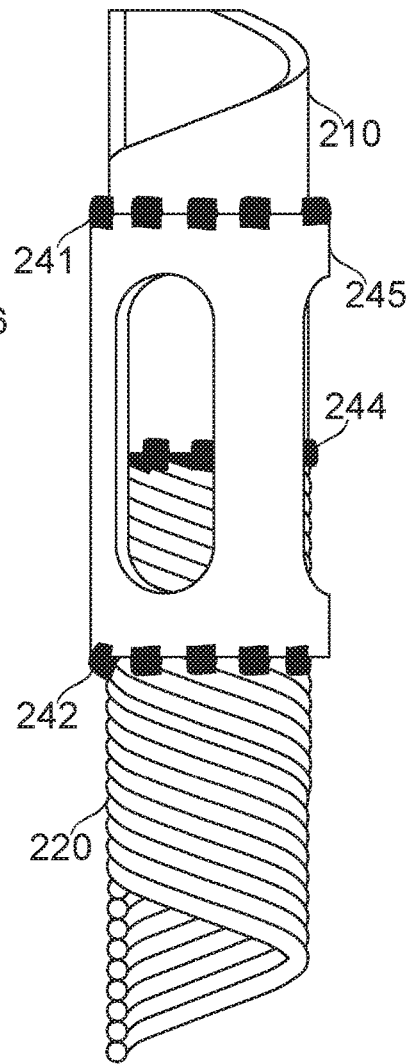
Figure 4F:
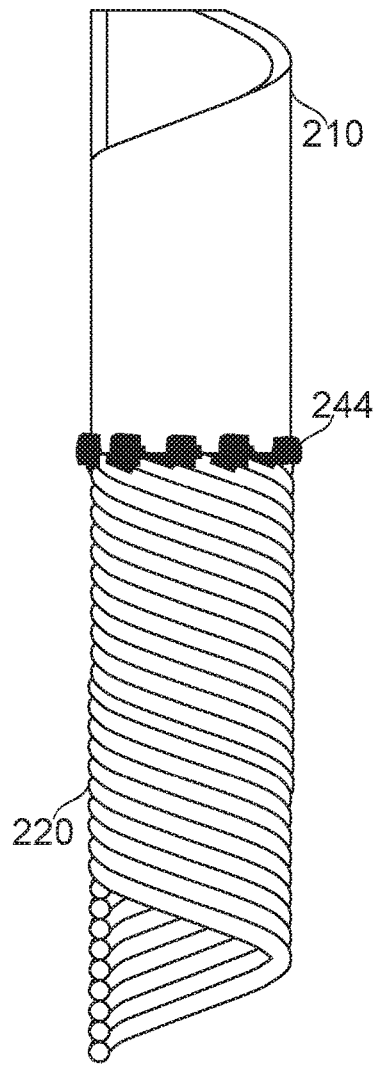

Reference is now made to FIGS. 4D-4F, which show alternative attachment configurations of a multihelix 220 and a proximal tube 210, according to some exemplary embodiments of the invention.

In FIG. 4D, a jig 245 is shown in position to align multihelix 220 with proximal tube 210. In some embodiments of the invention, welds 244 directly join multihelix 220 to proximal tube 210. In some embodiments, welds 244 are made through one or more apertures 246 of jig 245. Optionally, welds 244 directly join multihelix 220 and proximal tube 210. Optionally, welds include material of jig 245 (not shown), for example, extending along the wall of one or more apertures 246. In some embodiments, the apertures 246 are closed. In some embodiments, apertures 246 are open ended. In some embodiments, jig 245 is an apertured tube, for example, a tube such as connector 240, provided with one or more apertures through which one or more welds can be made. Optionally, the jig is rotated relative to the assembly to provide access to a plurality of welding regions through the one or more apertures. Optionally, jig 245 is welded to the multihelix 220 and/or proximal tube 210 by welds 242, 243 (FIG. 4E). In some embodiments, jig 245 is removed (for example, cut away) from the assembly after welding (FIG. 4F). In some embodiments, additional welds 244 are made after removal of the jig 245. In some embodiments, a reinforcement material is added with additional welding and/or adhesion, for example in the form of foil strips or wrapping, or one or more wires.

In some embodiments, jig 245 is another construction suitable for aligning the microcatheter parts, such as a clamp or slot. A potential advantage of removing a jig 245 after attachment of multihelix 220 and proximal tube 210 is to reduce an outer thickness at the join region. A potential advantage of an apertured jig 245 which remains attached to the assembled join region is to allow direct attachment through its body of the underlying multihelix 220 and proximal tube 210.

Tip Connection

Figure 5A:
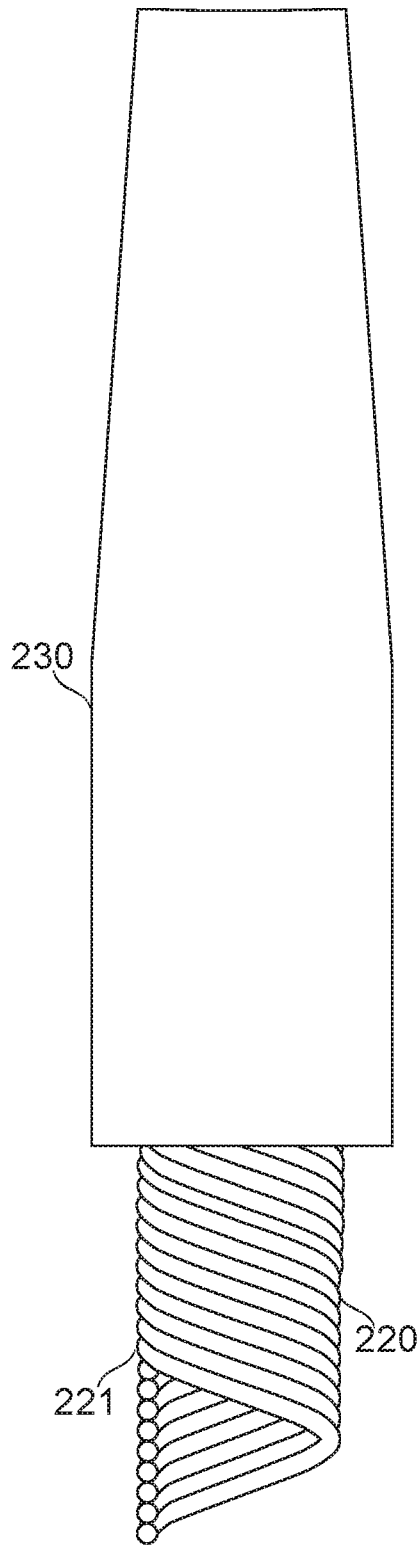
FIGS. 5A-5B schematically illustrate connection of a tip to the distal end of a multihelix, according to some exemplary embodiments of the invention.
Figure 5B:
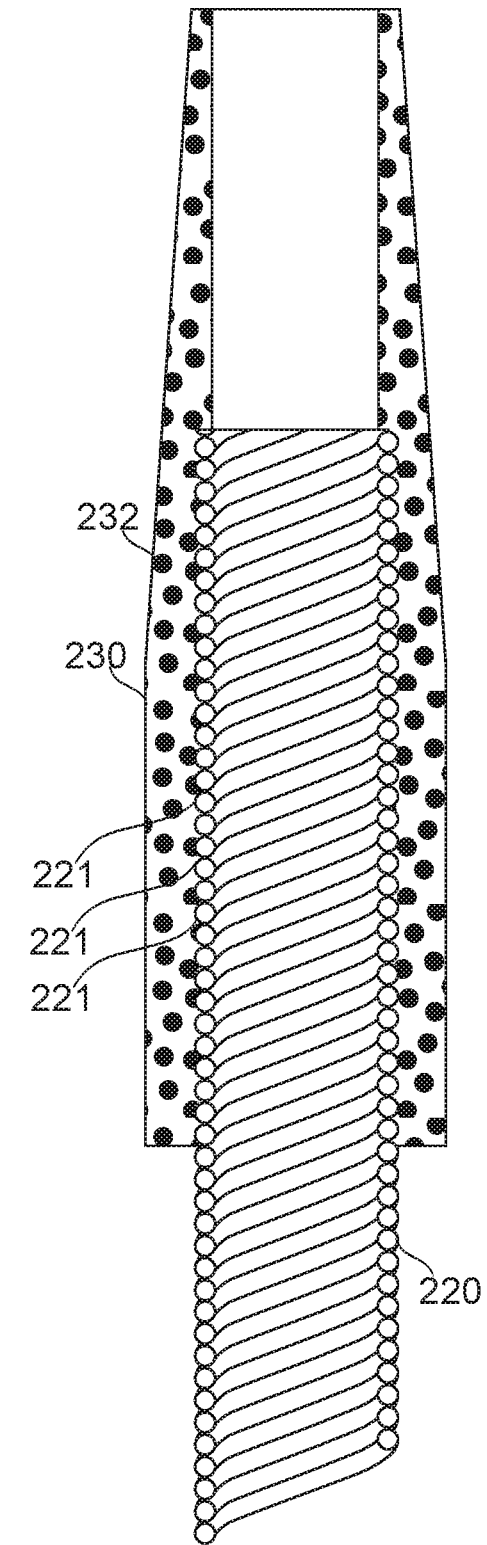

Reference is now made to FIGS. 5A-5B, which schematically illustrate connection of a tip 230 to the distal end of a multihelix 220, according to some exemplary embodiments of the invention.

In some embodiments of the invention, tip 230 comprises a tapering outer surface surrounding an inner lumen sized for the passage of a guidewire. Potentially, the taper provides an advantage for crossability, for example, by providing a smaller contact point which gradually broadens to lever a restriction apart as the tip passes. In some embodiments, the taper produces increased flexibility of the distal portion of tip 230. A more flexible tip in turn is a potential advantage for non-traumatic insertion and/or for navigability. In some embodiments, tip 230 comprises a relatively soft material, such as a polymer, for example Pebax®, polyamide, and/or silicone (Pebax® is a registered trademark of Arkema France Corporation). Potentially, construction from a soft material reduces the likelihood of traumatic injury by the tip of the microcatheter.

Figure 6:
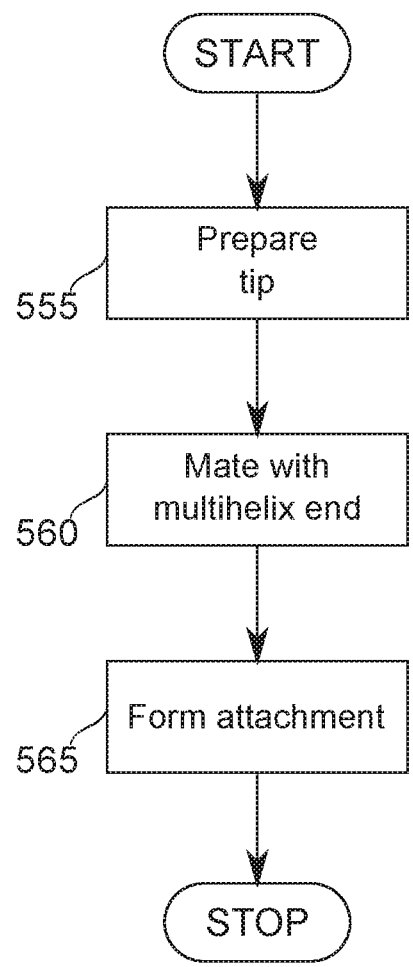
FIG. 6 is a flow chart describing in outline operations during tip attachment to a multihelix distal end, according to some exemplary embodiments of the invention.

Reference is now made to FIG. 6, which is a flow chart describing in outline operations during tip attachment to a multihelix distal end, according to some exemplary embodiments of the invention.

The flow chart begins, and at block 555, the tip is prepared for insertion over the wire. In some embodiments, tip 230 comprises radio-opaque material, for example, particles 232 of tungsten, tantalum and/or gold. Potentially, this allows the tip of the microcatheter lead to be observed, for example, under fluoroscopy. In some embodiments, the tip is prepared, for example, from a polymer tube, hot-molded together with impregnating radio-opaque material. In some embodiments, the tip is a commercially available tip, pre-impregnated with radio-opaque material. Optionally, tip 230 comprises a bend, which potentially directs an exiting guidewire to a lateral position, for example, to increase maneuverability and/or trackability. The bend may be imparted before or after tip attachment.

At block 560, the tip is mated to the multihelix end. At block 565, attachment is formed, and the flowchart ends. In some embodiments of the invention, attachment of tip 230 to multihelix 220 is by causing re-flow (for example under increased pressure and/or temperature), causing portions of tip 230 to intercalate between wire filars 221, producing a hold that resists movement of the tip 230 along the multihelix 220. In some embodiments, the re-flow temperature is within, for example, 5-10° C. of the melting point of the tip matrix material, 2-5° C., 1-3° C., or 0-10° C. A melting temperature for Pebax®, for example, is in the range of 130°-180° C. In some embodiments, the re-flow temperature is above a melting point in this range. In some embodiments, an adhesive matrix is used for tip adhesion.

Overtube and Navigability

Figure 7:
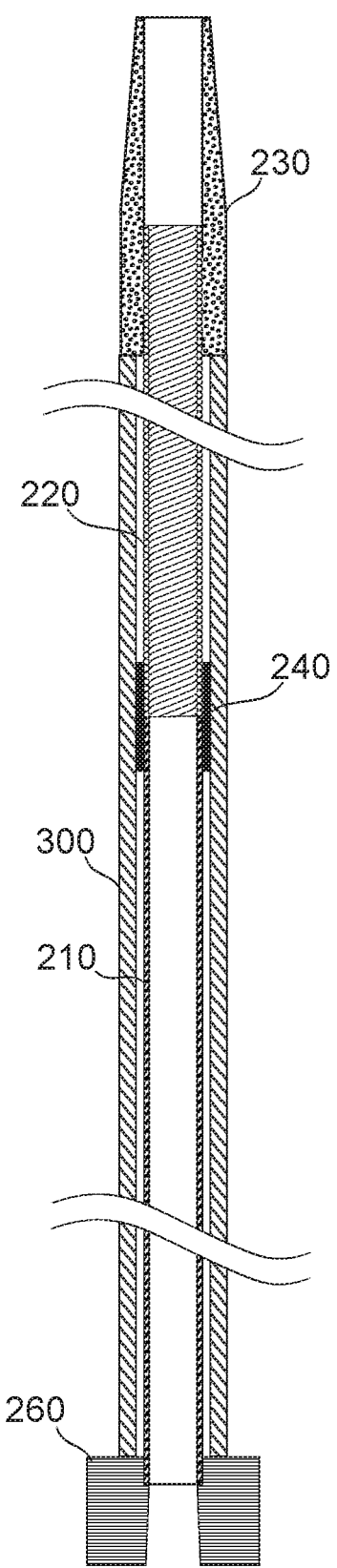
FIG. 7 shows a microcatheter assembly including an overtube over a joined multihelix and proximal tube assembly, according to some exemplary embodiments of the invention.

Reference is now made to FIG. 7, which shows a microcatheter assembly including an overtube 300 over a joined multihelix 220 and proximal tube 210 assembly, according to some exemplary embodiments of the invention.

In some embodiments of the invention, overtube 300 comprises a tube made of a polymer material, for example a polyamide (nylon-12, nylon-6,6), PTFE, polyethylene, and or polyolefin. In some embodiments, tube 300 is coated with a hydrophilic layer of a material known in the art—such as hyaluronic acid—for lubrication. Optionally, overtube 300 is secured to inner elements by an adhesive, such as a cyanoacrylate adhesive. In some embodiments, overtube 300 is of a heat-shrinkable material—for example, a thermoplastic such as polyester, nylon, polyolefin, or another suitable thermoplastic known in the art—and is shrunk over the inner components of the microcatheter to achieve a form fit with reduced diameter.

In some embodiments of the invention, overtube 300 comprises a reinforcing structure, known in the art, such as braided wires. Potentially, this improves pushability and/or torqueability.

In some embodiments, the proximal end of the microcatheter comprises a Luer-tapered connector 260 (or other standard connection) for receiving and/or closing off the proximal parts of proximal tube 210 and/or overtube 300.

Figure 8:
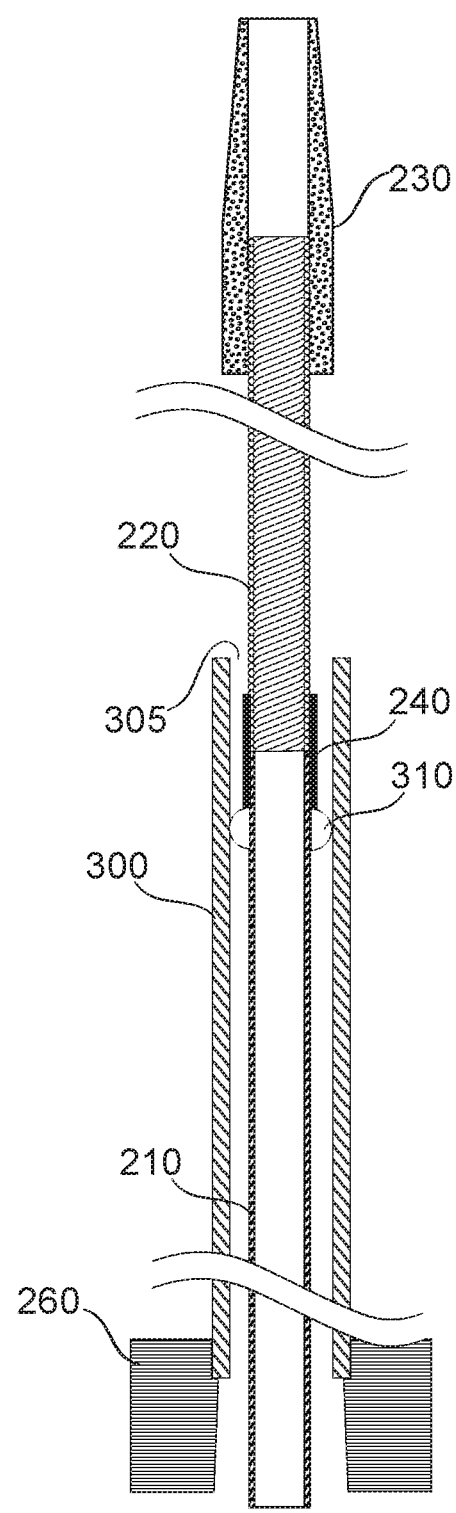
FIG. 8 shows a microcatheter assembly including an overtube slidably associated to a multihelix and proximal tube assembly, according to some exemplary embodiments of the invention.

Reference is now made to FIG. 8, which shows a microcatheter assembly including an overtube 300 slidably associated to a multihelix 220 and proximal tube 210 assembly, according to some exemplary embodiments of the invention.

It is a potential advantage to be able to adjust the mechanical properties of a distal portion of a microcatheter in the course of a procedure. For example, it is a potential advantage to adjust microcatheter stiffness to change the trade-off between pushability and navigability. In some embodiments of the invention, overtube 300 is slidably associated with the inner parts of the microcatheter, allowing, for example, multihelix 220 to alternately protrude for greater distal flexibility, and retract for greater pushability. In some embodiments, relative motion of the inner and outer tubes of the microcatheter is induced by manipulating the tubes near their proximal ends.

Microcatheters operating within a blood-filled environment are potentially subjected to capillary action and/or fluid pressure causing blood to force its way into the microcatheter. Blood that clots can then cause blockages or unwanted adherence of microcatheter parts. In particular, in some embodiments, the opening of a gap between the tip 230 and the overtube 300 may allow blood to enter the aperture of the overtube at 305 and begin to fill the tube. Potentially, the blood reaches all the way to the proximal end of the tube, where it may clot and jam relative motion of the overtube 300 and multihelix 220. The Inventors have found that, without countermeasures, the relative movement of inner and outer tubes can become increasingly difficult after 5-15 minutes of catheterization, potentially leading to immobilization.

In some embodiments, blood filling is restricted to a relatively short distal section of the tube by gasket 310. In some embodiments, gasket 310 is fitted tightly enough to proximal tube 210 (optionally, tube 220) to substantially prevent the passage of blood therebetween. In some embodiments, overtube 300 fits tightly enough to gasket 310 to substantially prevent the passage of blood therebetween. In some embodiments, substantial prevention of passage of blood comprises restricting the passage of blood sufficiently to permit a microcatheter procedure of, for example, 15 minutes, 30 minutes, or an hour, without seizing of the motion between overtube 300 and proximal tube 210 and/or multihelix 220. In some embodiments, blood is entirely prevented from passing the gasket. In some embodiments, blood passage is restricted to at most a layer sufficiently thin that a slide-preventing clot does not form.

The length of gasket 310 may be, for example, in the range of 0.5-2 mm, 1-2 mm, 1.5-3 mm, 2-4 mm, 3-6 mm, 5-10 mm, or another longer or shorter length. It is a potential advantage for the gasket 310 to be long enough to comprise enough cumulative resistance to substantially prevent the passage of blood beyond it. In contrast with this, it is a potential advantage for the gasket 310 to be short enough that it does not comprise a significant resistance to the relative motion of overtube 300 and the inner assembly comprising the multihelix 220 and/or proximal tube 210. In some embodiments, the range of gasket lengths described comprises a range of functional compromise between these two potential advantages.

In some embodiments, gasket 310 comprises a ring of a polymeric material, for example PTFE or silicone. It is a potential advantage for the gasket to be of a relatively low friction material (PTFE is such a material), so that it acts as a bearing for the relative motion of overtube 300 and multihelix 220 and/or proximal tube 210.

In some embodiments, gasket 310 is assembled to the microcatheter by sliding it over the free end of proximal tube 210 (optionally multihelix 220) before attachment between multihelix 220 and proximal tube 210 is made. It is a potential advantage to do so, as this allows placing gasket 310 a significant distance proximal to the distal end of the microcatheter without having to push it along the whole length of multihelix 220, avoiding potential damage and/or other difficulties of assembly.

Figure 9:
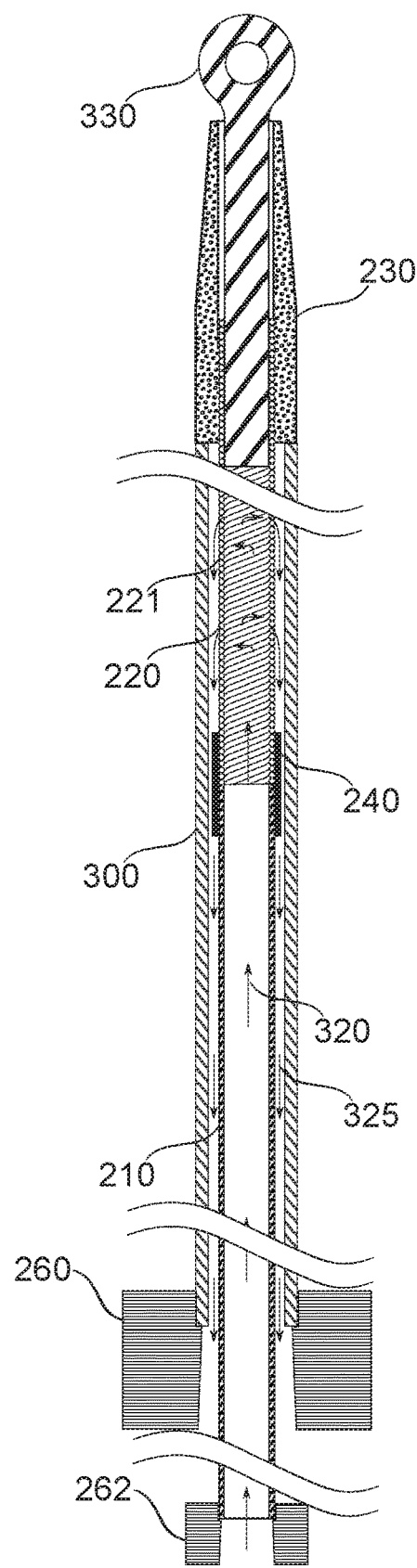
FIG. 9 shows anticoagulant perfusion of a microcatheter assembly including an overtube slidably associated to a multihelix and proximal tube assembly, according to some exemplary embodiments of the invention.

Reference is now made to FIG. 9, which shows anticoagulant perfusion of a microcatheter assembly including an overtube 300 slidably associated to a multihelix 220 and proximal tube 210 assembly, according to some exemplary embodiments of the invention.

In some embodiments of the invention, the locking effects of coagulated blood are mitigated by flushing the microcatheter with an anticoagulant solution, such as a standard solution of heparin in saline. Optionally, the flushing is into the proximal end of proximal tube 210 (for example, connected to an anticoagulant solution source using Leur connector 262). In some embodiments of the invention, plug 330 ensures that the anticoagulant fluid 320 flowing distally is forced through wire filars 221 upon reaching multihelix 220. In some embodiments, anticoagulant 325 then flows proximally, occupying the interstices between overtube 300 and multihelix 220 or proximal tube 210. Plug 330 is removable before microcatheter insertion to a body. During microcatheterization, the anticoagulant acts upon blood invading the flushed interstices to reduce clotting, preventing tube locking.

In some embodiments of the invention, surfaces liable to come into contact with blood are coated and/or lined with PTFE (Teflon®). Potentially, PTFE surfaces reduce thrombogenesis.

Figure 10:
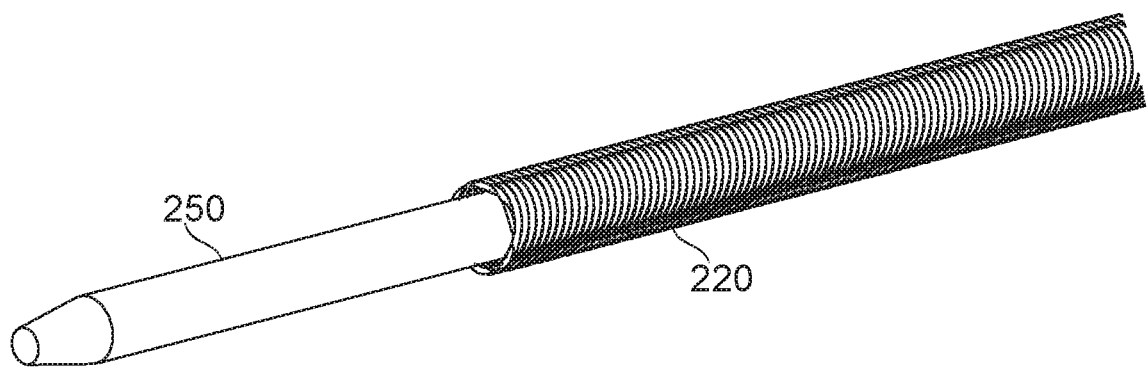
FIG. 10 shows an inner tube contained within a multihelix, according to some exemplary embodiments of the invention.

Reference is now made to FIG. 10, which shows an inner tube 250 contained within a multihelix 220, according to some exemplary embodiments of the invention.

In some embodiments of the invention, variable distal flexibility is obtained by using a flexible inner tube 250, which can be alternately protruded beyond the distal end of multihelix 220, or retracted. In some embodiments, inner tube 250 is formed of a polymer, for example PTFE or HPDE. It is a potential advantage for flexibility to protrude the flexible inner tube during navigation in order to navigate fine and/or tortuous vascular anatomy. Optionally, the multihelix 220 can be brought up behind the advanced inner tube 250 to provide support and/or pushability, for example to allow further advancement into the vasculature. This is a potential advantage, for example to allow retrograde approach to a lesion, where a microcatheter must be steered through tortuous vasculature (often comprising shunting vessels) to arrive at a lesion from a reversed angle of approach.

Overtube and Positioning

Figure 11A:
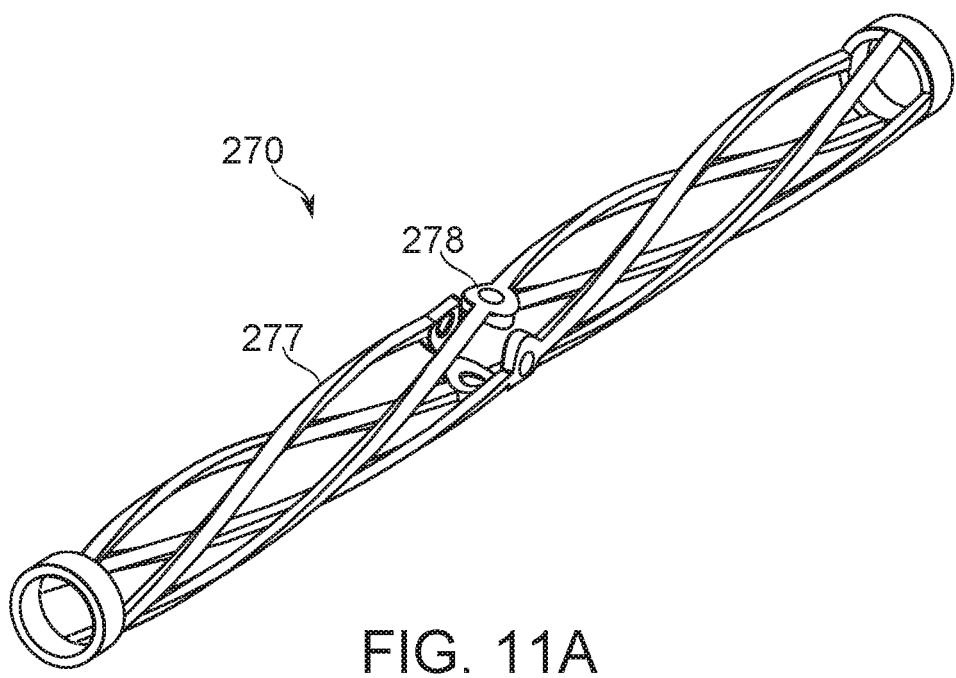
FIGS. 11A-11C schematically illustrate a microcatheter positioning device, according to some exemplary embodiments of the invention.
Figure 11B:
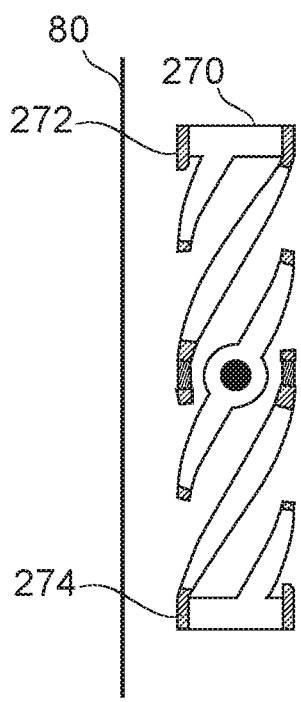
Figure 11C:
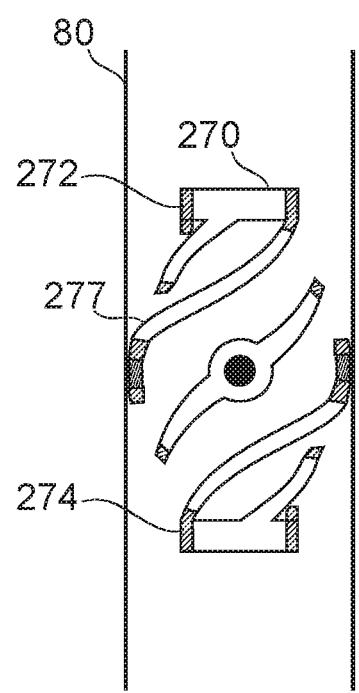
Figure 11D:
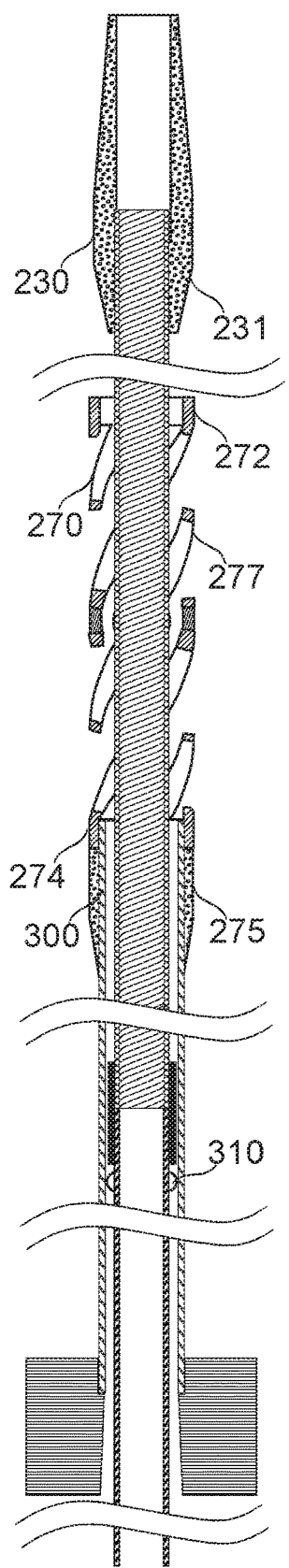
FIGS. 11D-11F show operation of a microcatheter configured for manipulation of a positioning device, according to some exemplary embodiments of the invention.
Figure 11E:
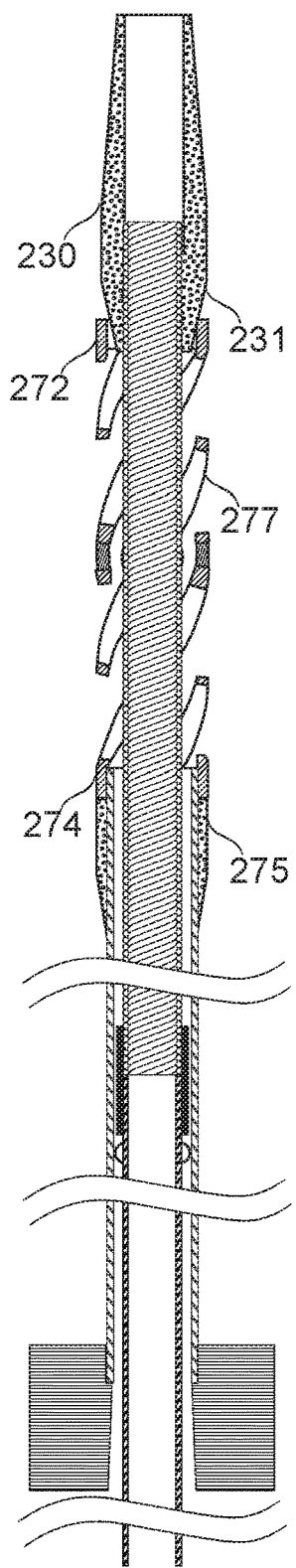
Figure 11F:
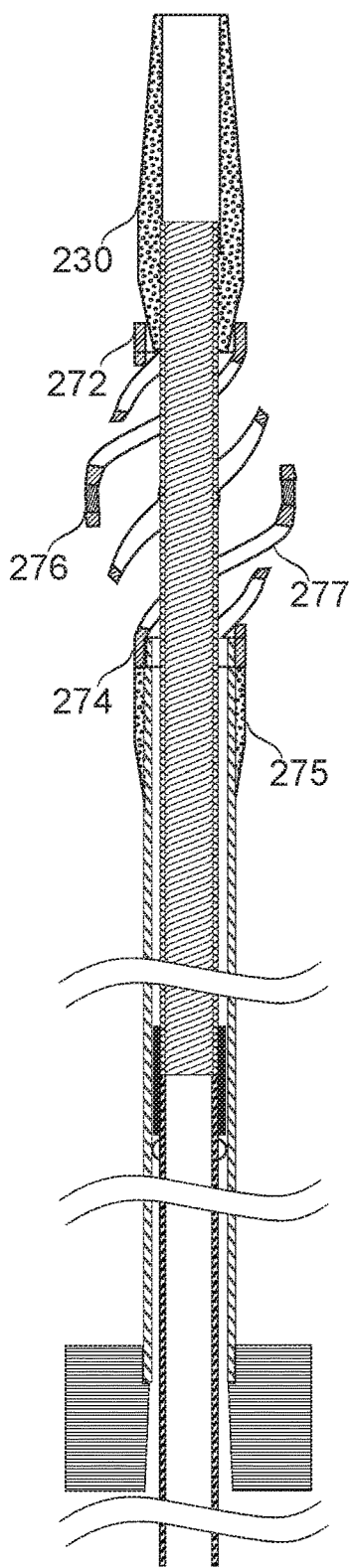

Reference is now made to FIGS. 11A-11C, which schematically illustrate a microcatheter positioning device 270, according to some exemplary embodiments of the invention. FIG. 11A is a perspective view; FIGS. 11B-11C are sectional views. Reference is also made to FIGS. 11D-11F, which show operation of a microcatheter configured for manipulation of a positioning device 270, according to some exemplary embodiments of the invention.

In some embodiments of the invention, positioning device 270 comprises at least one strut 277 configured to radially expand when proximal end 274 and distal end 272 are urged toward one another. The resulting expansion potentially constrains the relative positioning and/or points of contact between the microcatheter and a surrounding lumen wall 80 (such as an arterial wall). Optionally, the constraining places the positioning device 270 in a preconfigured relationship to the lumen wall, typically centering the device axis in the lumen. In some embodiments of the invention, at least one radio-opaque marker 276 is provided, allowing, for example, fluoroscopic monitoring of microcatheter positioning during a catheterization procedure.

The arrangements for sliding tubes described hereinabove are configured in some embodiments of the invention to allow operation of a centering element 270 in different insertion operating modes. In some embodiments, the positioning device 270 is anchored at a proximal end 274, for example by attachment to an overtube 300. In some embodiments, the distal region of overtube 300 comprises a ferrule 275 which participates in attachment. In some embodiments of the invention, there is no attachment at the proximal end 274; instead, for example, the widening at ferrule 275 blocks proximal movement of the centering element 270 by its shape.

In some embodiments of the invention, proximal end 272 of the positioning device 270 is left free. In some embodiments, tip 230 comprises a receiving surface 231 on its proximal side. Optionally, the receiving surface 231 is sloped. In some embodiments, ferrule 275 comprises a distal-facing receiving surface, optionally sloped. It is a potential advantage for the receiving surface 231 or the distal surface on ferrule 275 to be sloped, for movement proximally and/or laterally through the restricted space of a blood vessel, where a sharp edge may catch and/or cause injury during movement. In some embodiments, the slope is, for example, 5-10° relative to the catheter long axis, 10-20°, 15-25°, 20-30°, 35-45°, or another larger or smaller slope.

In a first operating mode (FIG. 11D) of some embodiments of the invention, the microcatheter tip 230 is extended distally from the insertion element. This configuration is used, for example, for navigation of the distal microcatheter region when flexibility is required.

In a second operating mode (FIG. 11E) of some embodiments of the invention, the positioning device has been brought up to the receiving surface 231 of tip 230, by relative axial motion of overtube 300 and multihelix 220. In this configuration, the distal region of the microcatheter is stiffened, potentially increasing pushability, for example in order to cross a constricted region. Additionally or alternatively, the positioning device is now in preparation for radial expansion. In some embodiments, tube lockup due to blood intrusion is prevented, for example by gasket 310 or anticoagulant pre-flushing.

In a third operating mode (FIG. 11F) of some embodiments of the invention, the positioning device has been radially expanded by relative axial motion of overtube 300 and multihelix 220 that compresses proximal end 274 closer to distal end 272 of the positioning device 270. In this configuration, the distal tip is potentially moved away from a vascular wall, allowing distal tip 230 and/or a guidewire passing out therefrom (not shown) to cross a vascular region nearer to the center of the lumen. This is a potential advantage, for example to cross vascular lesions where the best entry point to the lesion is central in the lumen.

Tip Support Rings

Reference is now made to FIGS. 12A-12D, which show support rings attached to a distal portion of a microcatheter multihelix (multifilar helix), according to some exemplary embodiments of the invention.

In some embodiments, ring 1202, 1204, 1206 is provided as part of the distal tip assembly of the catheter. Optionally, the ring 1202, 1204, 1206 comprises a radio-opaque substance, for example, gold, tantalum, and/or platinum.

In some embodiments, the ring 1202, 1204, 1206 serves to stabilize the wire ends of the multihelix.

Optionally, the ring is attached to the multihelix, for example by welded and/or adhesive fixation to the wire ends, or near the wire ends, such that it controls the positioning of the wire ends—for example, so that they do not protrude inward or outward to where they can potentially interfere with advancing the multihelix and/or advancing a guide-wire through the multihelix lumen. The multihelix length is optionally any length; for example, from the whole length of the microcatheter to a short distal segment (provided, for example, to give particular navigability to the tip). The multihelix 220 length in a trans-femoral cardiac procedure, for example, is about 30 cm. In some embodiments, multihelix 220 is 5-10 cm, 7-17 cm, 15-25 cm, 20-30 cm, 25-40 cm in length, or another longer or shorter length. The multihelix outer diameter is in the range, for example, of about 0.55-0.65 mm, 0.7-0.9 mm, 0.85-0.95 mm, 0.9-1.1 mm, or anther range having the same, larger, smaller, and/or intermediate bounds. Multihelix dimensions are also described, for example, in relation to FIG. 2A hereinabove.

In some embodiments, the ring serves to stabilize and/or anchor a tip 230 placed over the ring. The tip 230 comprises, for example, a material chosen to be soft enough for atraumatic operation (reducing the chance of injury during catheter tip movement), thin and/or pliable enough for navigability through small blood vessels, yet still stiff enough to advance without folding and/or collapse. It is a potential advantage to modulate these properties based on modulation of the tip wall thickness 230A, and tip overall diameter 230B, along the tip profile. Optionally, placement of the ring is distal to (rather than over) a multihelix. Optionally, this allows reduction of ring outer diameter. Optionally, reduction of ring outer diameter allows tip wall thickness 230A to be relatively increased and/or tip outer diameter 230B relatively reduced over regions of a ring 1204, 1206 which are relatively reduced in outer diameter. Potentially, stiffening conferred by a ring region helps to maintain tip 230 toward a more axial orientation, relative to a more flexible multihelix. Optionally, the tip extent 230C along a multihelix region is reduced according to the provision of an anchoring ring 1202, 1204, 1206. Potentially, providing a dimensionally stable anchoring region allows more reliable fixation for a shorter length of anchoring. A potential advantage of this is to preserve catheter flexibility: the stiff and/or thick portion of the tip 230 is optionally shorter, and/or the region of interference with multihelix 220 bending is shorter.

In some embodiments (FIG. 12A), ring 1202 is assembled to a distal portion of a multi-helical tube 220 by passage from the distal end a short distance over the outer diameter of the multihelix 220 to which an inner lumen 1210 of the ring 1202 is sized. Optionally, the ring 1202 is secured in place, for example, by gluing and/or laser welding. The distance passed is within the range, for example, of about 250-400 μm, 350-600 μm, 500-750 μm, 600-1000 μm, 250-1000 μm, or within another range having the same, larger, shorter, and/or intermediate bounds. In some embodiments, the distal terminus 1203 of the multihelix protrudes from the ring. In some embodiments, the distal terminus 1203 is within the ring. Optionally, absolute and relative multihelix 220 and ring 1202 diameter dimensions are, for example, as described for multihelix 220 and connector 240 in relation, for example, to FIG. 2A. The length of ring 1202, 1204, 1206 is within the range, for example, of about 250-400 μm, 350-600 μm, 500-750 μm, 600-1000 μm, 250-1000 μm, or within another range having the same, larger, smaller, and/or intermediate bounds. Optionally, ring length is chosen based on a degree of stiffness imparted to the tip region of the catheter, for example, longer to stiffen the tip, or shorter to allow the tip more pliability. Optionally, ring length is chosen to be longer to increase visualization of radio-opaque properties of the ring. Optionally, ring length is increased to more clearly indicate an orientation and/or scale of the catheter tip.

Optionally, the ring 1202 on the multihelix 220 comprises one or more anchor surfaces 1205. In some embodiments, a tip 230 is molded over at least a portion of ring 1202, such that anchor surfaces 1205 serve to block motion of the tip along the shaft of the multihelix in one or both axial directions. Optionally, the outer surface of ring 1202 is further shaped to block rotation and/or to enhance anchoring, for example as described in relation to the raised and/or cut regions of ring 1206 hereinbelow.

In some embodiments (FIGS. 12B, 12D), a ring 1204 is attached abutting the distal terminus 1203 of a multihelix 220. Optionally, the outer diameter 1212 of the ring 1204 is sized to be about the same as the outer diameter of the multihelix 220. In some embodiments, the outer diameter of the ring (optionally, the minimum outer diameter, and/or the maximum outer diameter) is in the range of 0.5-0.65 mm, 0.6-0.75 mm, 0.7-0.9 mm, 0.85-0.95 mm, 0.9-1.1 mm, or another range of diameters having the same, larger, smaller, and/or intermediate bounds. In some embodiments, the wall thickness of proximal tube 210 is, for example, 30-50 µm, 40-50 µm, 45-60 µm, 50-70 µm, 60-80 µm, or another larger or smaller wall thickness.

Optionally, sizing multihelix and ring to similar diameter permits (for example, relative to a ring 1202) the overall tip diameter to be kept small; for example, the maximum diameter of a tip 230 is chosen to be smaller for the same tip wall thickness 230A in an attachment region of the tip. Potentially, this assists in navigability by maintaining an overall reduced diameter. Optionally, absolute and relative multihelix 220 and ring 1204 dimensions are, for example, as described for multihelix 220 and tube 210 in relation, for example, to FIG. 2A.

Optionally, the inner diameter 1214 of the ring 1204 is sized to be about the same as the inner diameter of the multihelix 220. Potentially, this allows an insert (such as a guidewire) passing distally out through the multihelix 220 to exit through the ring 1204 without being interfered with by an exposed surface (jamming, for example). Optionally, end-abutted welding of the multihelix 220 and ring 1204 fixes the wire ends of multihelix 220 into place. Potentially, this prevents migration of the wire ends into a position where they can snag or otherwise interfere with the motion of a guide-wire or other internal structure.

In some embodiments (FIG. 12C), a ring 1206 having a textured outer surface is micro-welded to the end of a multihelix 220, substantially as for ring 1204. Abutting end laser welding of diameter-matched structures including a multihelix at the sub-millimeter scale is described, for example, in relation to FIG. 4F hereinabove.

Optionally, the outer surface of ring 1206 comprises raised regions 1207. Optionally, raised surfaces 1205, 1209 are positioned to interfere with the movement of a tip 230, potentially helping to lock tip 230 into place. The raised regions 1207 are optionally arranged around the outer surface of ring 1206 with radial symmetry (such as in the tooth-like pattern shown), as a pattern of knurling, as random bumps, or as any other pattern. In some embodiments, raised regions 1207 comprise one or more bumps, protrusions, holes, and/or slots.

In some embodiments, patterning of the raised regions 1207 comprises cutting away of material from ring 1206. In some embodiments, it is the raised regions which define a diameter of about the diameter of the multihelix 220, the walls of ring 1206 being thinned to a smaller diameter between the raised regions. A potential advantage of providing side surfaces 1209 in particular (the side surfaces being at least partially oriented longitudinally along the catheter axis) is to provide greater resistance to torquing motions. For example, the tendency of a tip 230 to twist relative to the rest of the distal catheter tip assembly is potentially reduced.

A potential advantage of the embodiment of FIG. 12C over that of FIG. 12A is that protrusion of the raised regions can be set to any degree sufficient for locking of the tip 230, without limitation to diameters large enough to structurally support the ring body itself, and/or without limitation to circumferentially uniform and/or circumferentially uninterrupted structures. Potentially, this allows greater freedom in the selection of the relationship between tip 230 wall thickness 230A and outer diameter 230B. Optionally, the raised regions 1207 protrude all the way through the tip 230 wall in one or more places. Optionally, the raised regions protrude to substantially thin the tip wall in one or more places, compared to the thickness over the lowest portion of the ring. The relative reduction in wall thickness is at least, for example, about 95%, 80%, 60%, 50%, 40%, 20%, or another greater, lesser or intermediate value. Optionally the raised regions are circumferentially incomplete. For example, the raised regions extend over no more than about 30°, 45°, 60°, 90°, or another greater, smaller, or intermediate radial extent of the ring. In some embodiments, the tip member tapers from a maximum wall thickness of, for example, 100-300 µm, to a minimum thickness of about 10 µm or less. Over a support ring, a tip (maximum) thickness is, for example, in the range of 50-100 µm, 80-150 µm, 100-200 µm, 150-300 µm, 150-400 µm, or another range having the same, larger, smaller, and/or intermediate bounds. An anchoring projection reduces tip wall width over a support ring to, for example, 0-10 µm, 0-50 µm, 20-100 µm, 80-150 µm, or another range having the same, larger, smaller, and/or intermediate bounds.

Integrity of the tip body 230 is optionally obtained by molding between and/or around (for example, both distal and proximal to) the raised regions 1207. Another potential advantage of ring 1206, in some embodiments, is to provide greater thickness leading to higher-contrast visualization of the ring 1206 in at least some of its portions (that is, in some embodiments, the radio-opacity of the ring is non-uniform). One potential use of this is direct or indirect visualization of rotational motions, as more and less radio-opaque regions alternately come into alignment with each other and/or an imaging axis. Potentially, this helps to verify that torque applied to a proximal end of the microcatheter is appropriately translated to distal tip motion. Potentially, this acts as a safety check; for example, to verify that rotational torque is not stored up along the length of the microcatheter and then suddenly released, raising the risk of injury.

In some embodiments, microwelding itself is used to provide outer-diameter texture to a ring 1202, 1204, 1206. The texture optionally comprises raised and/or excavated portions at the multihelix/ring joint. Optionally, the texture is added along the length of the ring, for example, by using laser welding to attach filler material along the ring body, and/or to ablate material along the ring body. Optionally, the filler material itself is chosen to be radio-opaque; comprising for example, an alloy comprising gold, tantalum, and/or platinum. In some embodiments, radio-opaque tip marking is provided by the use of laser welding of filler material to a multihelix away from, or without use of a ring.

It is expected that during the life of a patent maturing from this application many relevant microcatheter lumenal wall constructions will be developed and the scope of the terms multihelix and hypotube are intended to include all such new technologies a priori.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A microcatheter trackable through a mammalian vasculature, comprising:
   a hollow tubular metal member defining a first lumen section and having an external diameter sized to pass into a vascular lumen of less than 3 mm diameter; and
   a metallic helix defining a second lumen section;
   said metal member and said metallic helix each terminating in faces which abut around the face circumferences and are joined using a weld-join, and defining a passageway through said first and second lumen sections, said passageway unobstructed by sidewall obstructions from the weld-join; said passageway being sized for passage of a guidewire;
   a soft tip overlying a portion of said metallic helix and at least a portion of said metal member, said soft tip extending distally past said metallic helix and said metal member, said soft tip tapering in a distal direction away from a portion of said soft tip which overlies said metal member;
   wherein said weld-join comprises a plurality of weld spots on the exteriors of said metal member and said metallic helix, and holding the metal member and the metallic helix end-to-end at the abutting faces,
   said metal member and/or said weld points defining a plurality of raised regions around the outer surface of said metal member,
   said soft tip being molded on said plurality of raised regions, so that said plurality of raised regions is fittingly received by a body of said soft tip, and fixed thereto.

2. The microcatheter of claim 1, wherein the passageway through said first and second lumen sections comprises a metal surface.

3. The microcatheter of claim 1, comprising a connecting member overlaying said metal member and said metal helix, said connecting member defining a lumen containing portions of said metal member and said metallic helix.

4. The microcatheter of claim 3, wherein said connecting member is metal.

5. The microcatheter of claim 3, wherein the connecting member comprises a substantially cylindrical tube.

6. The microcatheter of claim 1, wherein said weld-join comprises a direct weld between said metal member and said metallic helix.

7. The microcatheter of claim 1, wherein said first and second lumen sections are sized for the passage therethrough by a tubular lining.

8. The microcatheter of claim 7, wherein said tubular lining extends from a proximal end of said metal member to a distal end of said metallic helix through said first and second lumen sections and through said passageway defined thereby.

9. The microcatheter of claim 8, wherein said tubular lining is a plastic polymer.

10. The microcatheter of claim 7, wherein said tubular lining defines a lumen sized for passage of a guidewire.

11. The microcatheter of claim 1, wherein said metallic helix comprises helically shaped metal wire.

12. The microcatheter of claim 11, wherein said metal wire is circumferentially coated by a plastic polymer.

13. The microcatheter of claim 1, wherein said metallic helix comprises a plurality of helically shaped wire filars, and wherein ends of said helically shaped wire filars abutting said metal member are attached to one another by welding.

14. The microcatheter of claim 13, wherein all of said ends of said helically shaped wire filars remain outside a diameter of said first lumen section at the region of abutting attachment.

15. The microcatheter of claim 13, wherein said second lumen section has a passageway defined by most interior portions of said helically shaped wire filars, a smallest diameter of said passageway being substantially unchanged or increasing in axial cross-sections leading up to an end of said second lumen section at an axial position of said weld-join.

16. The microcatheter of claim 1, wherein portions of said first and second lumen sections are axially aligned with one another at said weld-join, having lumen diameters within 10% of one another at said weld-join.

17. The microcatheter of claim 1, wherein said plurality of raised regions comprises a radio-opaque material.

18. The microcatheter of claim 1, wherein the plurality of raised regions comprises a ring of projections, and wherein a first thickness of a wall of said soft tip which overlies said projections is less than 50% of a second thickness of a wall of said soft tip which overlies the ring and away from said projections.

19. The microcatheter of claim 1, wherein the plurality of raised regions is circumferentially incomplete.

20. The microcatheter of claim 1, wherein the abutting faces of said metal member and said metallic helix are each a terminal face oriented to face perpendicular to a longitudinal axis extending between the metal member and the metallic helix.

21. The microcatheter of claim 1, wherein said plurality of raised regions are formed by provision of one or more apertures in said metal member.

* * * * *